United States Patent
Sexton et al.

(10) Patent No.: US 12,188,948 B2
(45) Date of Patent: *Jan. 7, 2025

(54) METABOLITE BIOMARKERS FOR DISEASES ASSOCIATED WITH THE CONTACT ACTIVATION SYSTEM

(71) Applicant: Takeda Pharmaceutical Company Limited, Osaka (JP)

(72) Inventors: Daniel J. Sexton, Melrose, MA (US); Malini Viswanathan, Acton, MA (US); Ryan Faucette, Melrose, MA (US); Tripti Gaur, South Grafton, MA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/728,285

(22) Filed: Apr. 25, 2022

(65) Prior Publication Data

US 2022/0365101 A1 Nov. 17, 2022

Related U.S. Application Data

(63) Continuation of application No. 16/333,101, filed as application No. PCT/US2017/051755 on Sep. 15, 2017, now Pat. No. 11,340,237.

(60) Provisional application No. 62/518,367, filed on Jun. 12, 2017, provisional application No. 62/395,770, filed on Sep. 16, 2016.

(51) Int. Cl.
*G01N 33/68* (2006.01)
*G01N 33/74* (2006.01)
*G01N 33/82* (2006.01)
*G01N 33/92* (2006.01)
*G01N 33/94* (2006.01)

(52) U.S. Cl.
CPC ..... *G01N 33/6893* (2013.01); *G01N 33/6806* (2013.01); *G01N 33/743* (2013.01); *G01N 33/82* (2013.01); *G01N 33/92* (2013.01); *G01N 33/942* (2013.01); *G01N 2800/224* (2013.01); *G01N 2800/50* (2013.01); *G01N 2800/52* (2013.01); *G01N 2800/7095* (2013.01)

(58) Field of Classification Search
CPC ......... G01N 33/6893; G01N 2800/224; G01N 2800/50; G01N 2800/52
See application file for complete search history.

(56) References Cited

U.S. PATENT DOCUMENTS

| | | | |
|---|---|---|---|
| 7,645,759 B2 | 1/2010 | Felicetti et al. |
| 8,951,739 B2 | 2/2015 | Kawamura et al. |
| 9,127,024 B2 | 9/2015 | Chellappan et al. |
| 11,340,237 B2 | 5/2022 | Sexton et al. |
| 2007/0192882 A1 | 8/2007 | Dewald |
| 2007/0218047 A1 | 9/2007 | Golz et al. |
| 2008/0031816 A1 | 2/2008 | Keller |
| 2008/0038276 A1 | 2/2008 | Sinha et al. |
| 2010/0028264 A1 | 2/2010 | Golz et al. |
| 2010/0034805 A1 | 2/2010 | Ladner et al. |
| 2010/0081136 A1 | 4/2010 | Golz et al. |
| 2010/0104501 A1 | 4/2010 | Golz et al. |
| 2010/0105076 A1 | 4/2010 | Perollier et al. |
| 2011/0098993 A1 | 4/2011 | Mas Benavente et al. |
| 2011/0111394 A1 | 5/2011 | Golz et al. |
| 2012/0003158 A1 | 1/2012 | Alexander et al. |
| 2012/0040383 A1 | 2/2012 | Jia et al. |
| 2013/0023056 A1 | 1/2013 | Raftery et al. |
| 2014/0086825 A1 | 3/2014 | McFaul |
| 2018/0298110 A1 | 10/2018 | Chyung et al. |
| 2019/0361036 A1 | 11/2019 | Sexton et al. |

FOREIGN PATENT DOCUMENTS

| | | | | |
|---|---|---|---|---|
| CN | 102077094 A | 5/2011 | | |
| CN | 104768560 A | 7/2015 | | |
| CN | 105873951 A | 8/2016 | | |
| EP | 2884282 A1 * | 6/2015 | ......... | G01N 33/6806 |
| JP | 2012-211908 A | 11/2012 | | |
| JP | 2013-509593 A | 3/2013 | | |
| JP | 2016-511394 A | 4/2016 | | |
| JP | 2016-511823 A | 4/2016 | | |
| JP | 2017-181322 A | 10/2017 | | |
| KR | 10-2012-0101038 A | 9/2012 | | |
| WO | 2007/044860 A2 | 4/2007 | | |
| WO | 2008/046508 A1 | 4/2008 | | |
| WO | 2008/046510 A1 | 4/2008 | | |
| WO | 2008/046528 A1 | 4/2008 | | |
| WO | 2011/053831 A1 | 5/2011 | | |
| WO | 2011/061304 A1 | 5/2011 | | |
| WO | 2014/159637 A1 | 10/2014 | | |
| WO | 2015/061183 A1 | 4/2015 | | |
| WO | 2016/049044 A1 | 3/2016 | | |
| WO | 2017/027771 A1 | 2/2017 | | |
| WO | 2018/053244 A1 | 3/2018 | | |
| WO | 2018/053260 A1 | 3/2018 | | |

OTHER PUBLICATIONS

Hack (Gut 1998 vol. 42, p. 485-492). (Year: 1998).*
Cugno et al., Plasma biomarkers of acute attacks in patients with angioedema due to C1-inhibitor deficiency. Allergy. Feb. 2009;64(2):254-7. doi: 10.1111/j.1398-9995.2008.01859.x. Epub Dec. 4, 2008.
Farkas et al., "Nuts and Bolts" of Laboratory Evaluation of Angioedema. Clin Rev Allergy Immunol. Oct. 2016;51(2):140-51. doi: 10.1007/s12016-016-8539-6.
Shang et al., UHPLC/Q-TOF MS-based plasma metabolic profiling analysis of the bleeding mechanism in a rat model of yeast and ethanol-induced blood heat and hemorrhage syndrome. J Pharm Biomed Anal. Apr. 2014; 92:26-34. Epub Dec. 27, 2013.

(Continued)

*Primary Examiner* — Changhwa J Cheu
(74) *Attorney, Agent, or Firm* — Wolf, Greenfield & Sacks, P.C.

(57) ABSTRACT

Provided herein are methods and kits for analyzing a biological sample obtained from a subject having, suspected of having, or being at risk for a disease associated with the contact activation system.

18 Claims, 3 Drawing Sheets
Specification includes a Sequence Listing.

(56) References Cited

OTHER PUBLICATIONS

Thon et al., Lack of dehydroepiandrosterone in type I and II hereditary angioedema and role of danazol in steroid hormone conversion. Allergy. Nov. 2007;62(11):1320-5. doi: 10.1111/j.1398-9995.2007.01477.x.
Wu, Contact pathway of coagulation and inflammation. Thromb J. May 6, 2015;13:17. doi: 10.1186/s12959-015-0048-y.
Czaller et al., Thyroid hormones and complement parameters in hereditary angioedema with C1-inhibitor deficiency. Ann Allergy Asthma Immunol. Aug. 2016;117(2):175-9. doi: 10.1016/j.anai.2016.06.005. Epub Jun. 28, 2016.

* cited by examiner

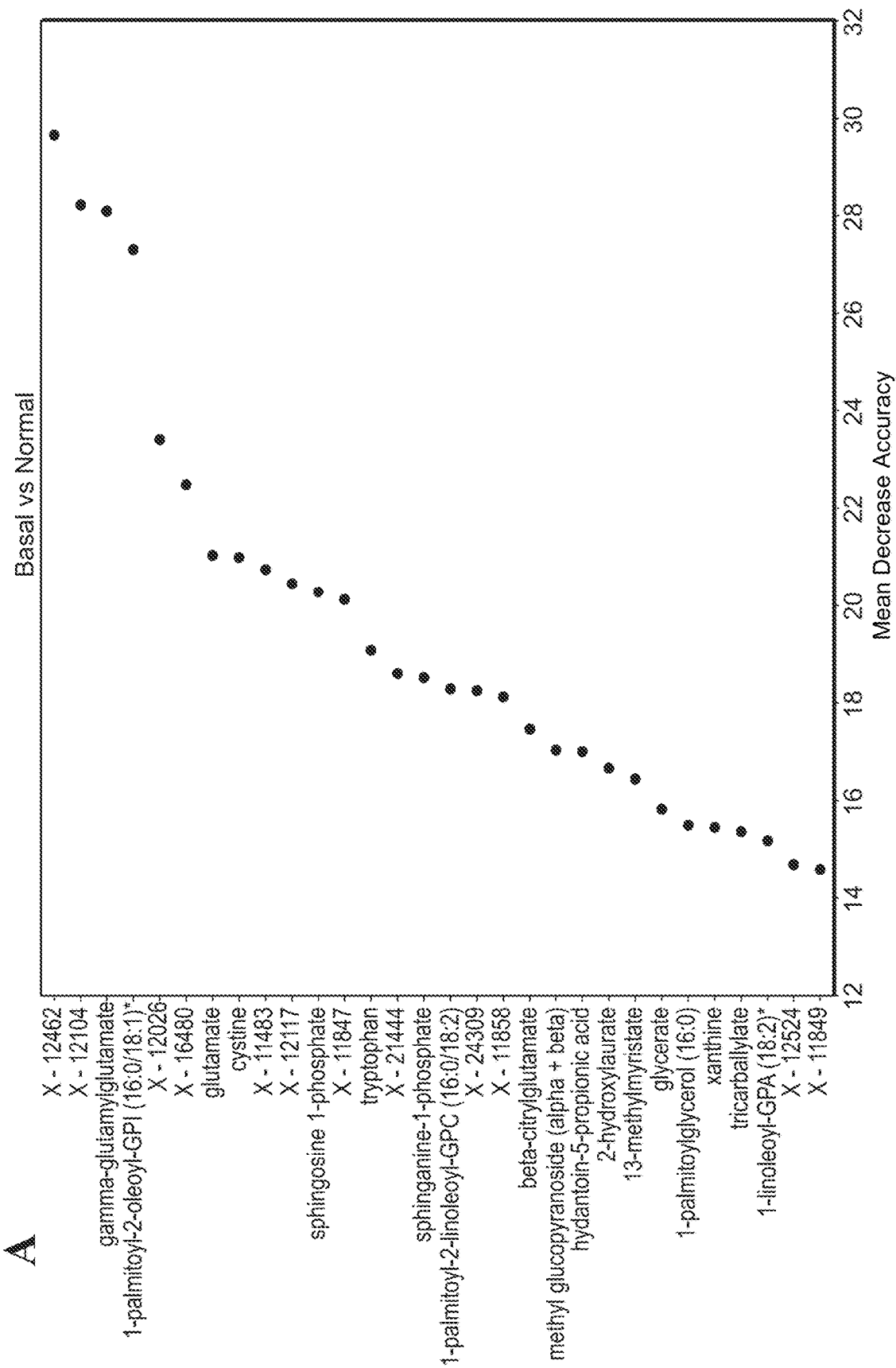

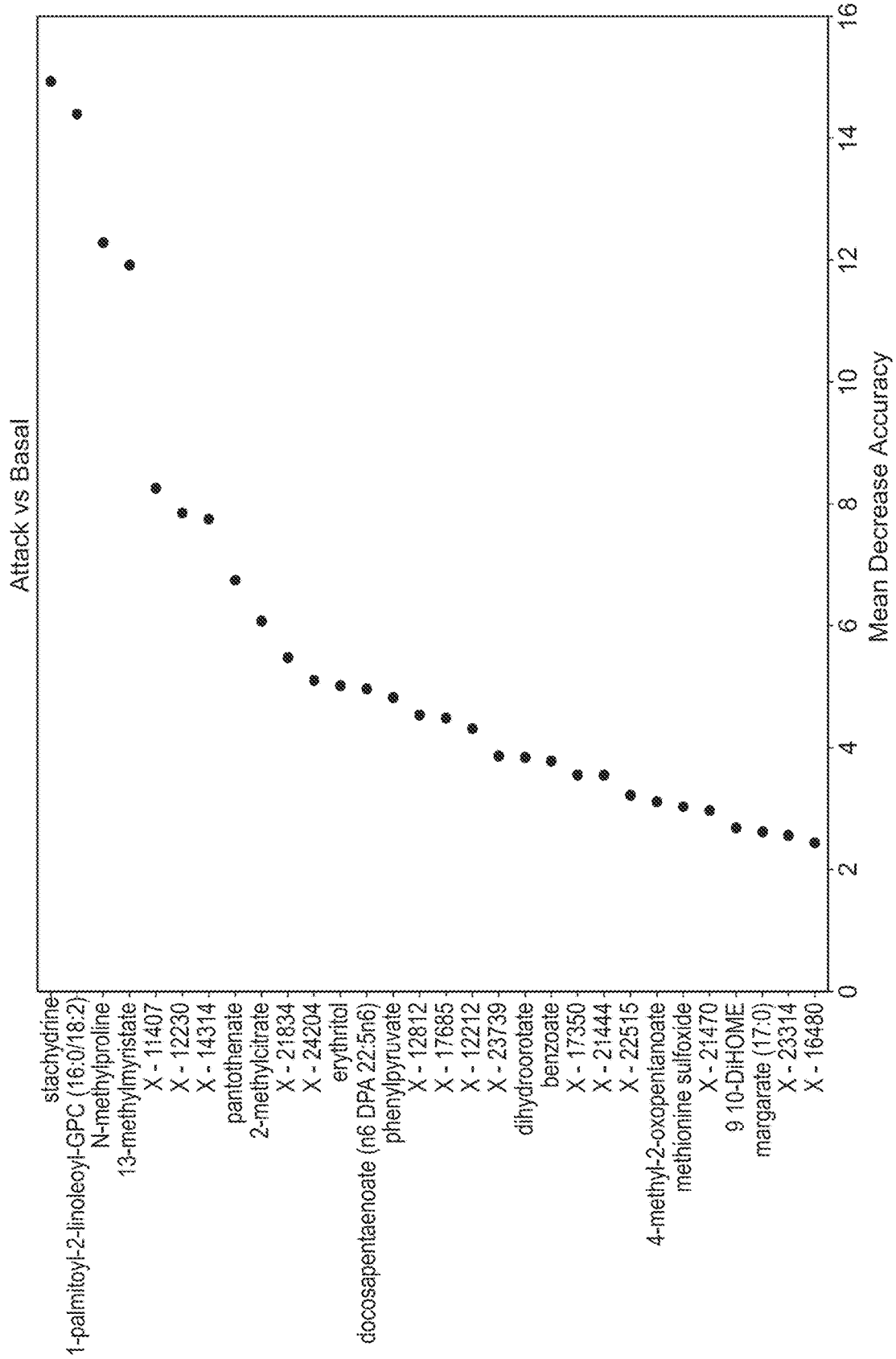

METABOLITE BIOMARKERS FOR DISEASES ASSOCIATED WITH THE CONTACT ACTIVATION SYSTEM

CROSS REFERENCE TO RELATED APPLICATIONS

This application is a continuation of U.S. application Ser. No. 16/333,101, filed Mar. 13, 2019, which is a national stage filing under 35 U.S.C. § 371 of international application number PCT/US2017/051755, filed Sep. 15, 2017, which claims the benefit under 35 U.S.C. § 119(e) of U.S. provisional application No. 62/518,367, filed Jun. 12, 2017 and U.S. provisional application No. 62/395,770, filed Sep. 16, 2016. The entire contents of each of these referenced applications are incorporated by reference herein.

BACKGROUND

The plasma contact activation system is a pro-inflammatory and pro-coagulant system involving a group of plasma proteases. It is activated by either factor XIIa upon exposure to foreign or negatively charged surfaces or on endothelial cell surfaces by prolylcarboxypeptidases (Sainz I. M. et al., *Thromb. Haemost.* (2007) 98, 77-83). Inappropriate or unregulated activation of the contact system has been implicated in various diseases, including hereditary angioedema (HAE).

HAE is a disease that causes episodic attacks of swelling, which can affect multiple parts of the body such as the face, extremities, genitals, GI tract and upper airways. Because HAE symptoms often resemble symptoms of allergies or intestinal colics, HAE patients are often difficult to identify until they exhibit severe or life-threatening symptoms. Early diagnosis would allow for better management of emergency situations involving acute HAE attacks and would also help manage HAE patients to prevent or dampen acute HAE episodes, e.g., allowing an HAE sufferer to avoid exposure to stimuli that might trigger HAE episodes.

It is therefore of great interest to identify biomarkers for HAE and develop reliable diagnostic and prognostic methods for identifying subjects having certain types of HAE or being at risk of suffering an acute HAE attack. Such biomarkers would also benefit the studies on disease mechanisms, which could facilitate the development of effective new therapies for the disease.

SUMMARY OF THE PRESENT DISCLOSURE

The present disclosure is based on the identification of metabolite biomarkers that are differentially present in biological samples obtained from subjects having diseases associated with the contact activation system as compared to healthy individuals or differentially present in biological samples obtained from subjects in different stages of such a disease (e.g., attack versus quiescence).

Accordingly, one aspect of the present disclosure provides methods of analyzing a sample comprising (i) providing a biological sample (e.g., serum sample or a plasma sample) obtained from a subject, such as a human subject, having, suspected of having, or being at risk for a disease associated with the contact activation system; and (ii) measuring the level of a metabolite biomarker set, which comprises at least one metabolite biomarker selected from Table 1. In some embodiments, the disease associated with the contact activation system is hereditary angioedema (HAE), such as type 1 HAE or type II HAE. In some instances, the biomarker set consists of 2-10 metabolite biomarkers selected from Table 1.

In any of the methods described herein, the at least one metabolite is serotonin or a metabolite associated with serotonin metabolism. In some embodiments, the at least one metabolite biomarker is a metabolite associated with fatty acid amide hydrolase activity (e.g., a fatty acid amide, such as palmitic amide, oleamide, or linoleamide). In some embodiments, the at least one metabolite biomarkers is a lipid peroxide (e.g., 9-hydroxyoctadecadienoic acid (9-HODE), 13-hydroxyoctadecadienoic acid (13-HODE), 9,10-di-hdroxy-12Z-octadecenoic acid (9, 10-DiHOME), 12,13-dihydroxy-9Z-octadecenoic acid (12,13-DiHOME), or 19,20-dihydroxy-4Z,7Z,10Z,13Z,16Z-docosapentaenoic acid (19, 20 DiHDPA)). In some embodiments, the at least one metabolite biomarker is a metabolite involved in sulfur metabolism (e.g., N-acetylmethionine, methionine sulfone, S-adenosylhomocysteine, cystine, or cysteine sulfinic acid). In some embodiments, the at least one metabolite biomarker is a metabolite involved in steroid metabolism (e.g., pregnenolone sulfate; 5 alpha-pregnan-3beta,20beta-diol monosulfate; pregnen-diol disulfate; pregn steroid monosulfate; prenanediol-3-glucuronide; cortisol; corticosterone; cortisone; dehydroisoandrosterone sulfate (DHEA-S); 16a-hydroxy DHEA 3-sulfate; epiandrosterone sulfate; androsterone sulfate; 4-androsten-3beta, 17beta-diol monosulfate; 4-androsten-3alpha, 17alpha-diol monosulfate; 4-androsten-3beta, 17beta-diol disulfate; 5alpha-androstan-3alpha, 17alpha-diol monosulfate; 5alpha-androstan-3beta,17-beta-diol disulfate; andro steroid monosulfate, etiocholanolone glucuronide or pregnanolone/alloprenanolone sulfate). In some embodiments, the at least one metabolite biomarker is a fatty acid (e.g., eicosapentaenoate (EPA), mead acid, or stearidonate). In some embodiments, the at least one metabolite biomarker is a cofactor precursor (e.g., a coenzyme A cofactor precursor, such as nicotinamide or pantothenate).

In some embodiments, the measuring the level of a biomarker set involves mass spectrometry, chromatography, or an immunoassay. In some embodiments, the measuring the level of a biomarker set involves mass spectrometry and wherein the biological sample is subjected to a separation step prior to the mass spectrometry (e.g., gas chromatography, liquid chromatography, or capillary electrophoresis).

In some embodiments, the method further comprises identifying the subject as having a disease associated with the contact system, if the level of the biomarker set of the subject deviates from the level of the same biomarker set of a control subject. In some embodiments, the method further comprises administering to the subject an effective amount of a therapeutic agent for treating the disease, such as a plasma kallikrein (pKal) inhibitor, a bradykinin 2 receptor inhibitor, and/or a C1 esterase inhibitor, if the subject is identified as having the disease. In some embodiments the pKal inhibitor is an anti-pKal antibody. In some embodiments, the therapeutic agent is lanadelumab, ecallantide, icatibant, or human plasma-derived C1 esterase inhibitor.

In some embodiments, the subject is a human patient who is on a treatment for the disease, and wherein the method further comprises assessing the efficacy of the treatment based on the level of the metabolite biomarker set, a deviation of the metabolite biomarker set level of the subject from that of a control subject being indicative of the treatment efficacy. In some embodiments, the method further comprises identifying a suitable treatment for the subject based on the level of the metabolite biomarker set. In some embodiments, the method further comprises identifying the subject as a candidate for a treatment of the disease based on the level of the metabolite biomarker set.

In some embodiments, the human patient has a history of the disease (e.g., HAE). In some embodiments, the metabolite biomarker set comprises one or more metabolite biomarkers selected from the list consisting of corticosterone, eicosapentaenoate, mead acid, stearidonate, nicotinamide, and pantothenate. In some embodiments, the method further comprises assessing the risk of disease attack (e.g., HAE attack) based on the level of the metabolite biomarker set, a deviation of the metabolite biomarker set level from that of a control subject being indicative of the risk of disease attack. In some embodiments, the method further comprises administering a therapeutic agent to the subject, if the subject is identified as at risk of disease attack.

The present disclosure provides biomarkers capable of identifying patients with diseases associated with the contact activation system (e.g., HAE). Measuring the levels of the biomarker sets may also be useful in the evaluation and treatment of such diseases.

Another aspect of the present disclosure provides methods of identifying a subject as having or at risk of having a disease associated with the contact activation system, the method comprising (i) providing a biological sample obtained from the subject; (ii) measuring the level of a metabolite biomarker set; and (iii) identifying the subject as having or at risk of having the disease if the level of the metabolite biomarker set deviates from the level of the metabolite biomarker set in a control sample.

Other aspects provide methods of assessing the risk of attack of a disease associated with contact system activation (e.g., HAE attack), the method comprising (i) providing a biological sample obtained from the subject; (ii) measuring the level of a metabolite biomarker set; and (iii) identifying the subject as at risk of having a disease attack if the level of the metabolite biomarker set deviates from the level of the metabolite biomarker set in a control sample.

In another aspect, a kit is provided for analyzing a sample of a subject having, suspected of having, or at risk for a disease associated with the contact system, the kit comprising a first binding agent specific to a first metabolite marker selected from Table 1; and a second binding agent specific to a second metabolite marker selected from Table 1; wherein the first metabolite marker and the second metabolite marker are different. In some embodiments, the kit further comprises at least one addition binding agent to another metabolite marker selected from Table 1. In some examples, the first binding agent is an antibody specific to the first metabolite biomarker and/or the second binding agent is an antibody specific to the second metabolite biomarker. In some embodiments, the kit may further comprise a first detection agent that binds to the first binding agent and a second detection agent that binds to the second binding agent. In some embodiments, the first binding agent and the second binding agent are immobilized on a support member.

The details of one or more embodiments of the present disclosure are set forth in the description below. Other features or advantages of the present disclosure will be apparent from the following drawings and detailed description of several embodiments, and also from the appended claims.

BRIEF DESCRIPTION OF DRAWINGS

The following drawings form part of the present specification and are included to further demonstrate certain aspects of the present disclosure, which can be better understood by reference to one or more of these drawings in combination with the detailed description of specific embodiments presented herein.

FIG. 1 presents graphs showing metabolite analysis results obtained from healthy control subjects and HAE patients, either during an attack or in basal state, by random forest analysis. A: patients having HAE at basal state were separated from healthy individuals with 77.5% accuracy from random forest analysis. B: patients having HAE at basal state were separated from patients having HAE during an attack with 20% accuracy.

DETAILED DESCRIPTION

Figure 2:
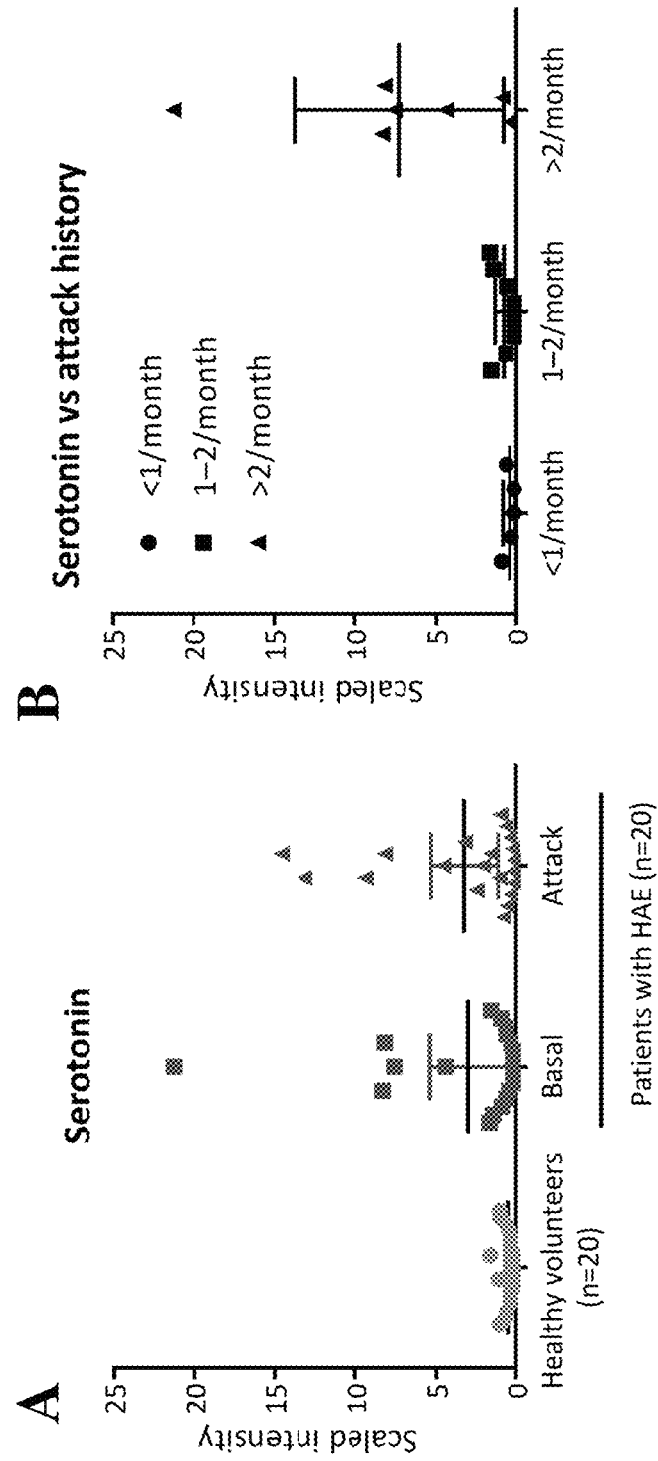
FIG. 2 presents graphs showing serotonin levels detected in plasma samples from patients having HAE (type I/type II) and from healthy volunteers. A: a diagram showing serotonin levels detected in plasma samples from patients having HAE (type I/type II; n=20) compared to and healthy volunteers (n=20). B: a chart showing serotonin levels detected in plasma samples from HAE patients at basal state (n=20) grouped based on HAE attack history (less than 1 time per month, 1-2 times per month, or more than 2 times per month). Serotonin levels are presented as fold increase over serotonin levels in healthy volunteers (n=20).

The contact activation system initiates the intrinsic pathway of coagulation and promotes inflammation through the release of the proinflammatory peptide bradykinin. Factor XII (FXII), also known as Hageman Factor, is a serine protease that plays a role in activation of the intrinsic pathways of coagulation as well as the kallikrein-kinin system. FXII is activated by negatively charged surfaces (e.g., polyanionic surfaces, glass, polyphosphate, ellagic acid) to produce the active form FXIIa. Activated FXIIa has the ability to cleave pre-kallikrein, generating active pKal. Subsequently, activated pKal is able to cleave FXII into FXIIa, resulting in a positive feedback loop in which FXIIa generates even more pKal, which further activates additional FXII into FXIIa. Activated pKal is also able to cleave high molecular weight kininogen (HMWK) to release bradykinin. In diseases associated with contact system activation, such as HAE, increased levels of bradykinin can induce vasodilation and inflammation that result in edematous HAE attacks. It is desired to identify novel biomarkers that can be used, for example, to identify diseases as mediated by the contact activation system, identify subjects having or being at risk of having such a disease.

The present disclosure is based, at least in part, on the identification of metabolites that are differentially present in biological samples obtained from subjects having diseases associated with the contact activation system (e.g., basal or attack) as compared to healthy individuals via metabolomic analysis. It was unexpectedly observed that metabolites belonging to particular cellular pathways or processes (e.g., metabolites involved in sulfur metabolism, steroid metabolism, serotonin metabolism, associated with fatty acid amide hydrolase activity) and metabolites belonging to metabolite families (e.g., fatty acids) had similar trends (e.g., elevated or reduced levels) in samples from subjects having the disease as compared to healthy individuals. Furthermore, several metabolites were identified as differentially present in biological samples obtained from subjects during an attack of a disease of the contact activation system as compared to subjects having the disease at quiescent (basal) state.

Accordingly, provided herein are methods for analyzing biological samples from subjects having, suspected of having, or being at risk for a disease associated with the contact activation system (e.g., HAE) by detecting the presence or measuring the level of a metabolite biomarker set. Such methods may be useful, e.g., for identifying patients who are at risk of a disease associated with the contact activation system (e.g., HAE), selecting a candidate for treatment, monitoring disease progression or disease state, assessing the efficacy of a treatment against a disease, determining a course of treatment, assessing whether a subject is at risk for an attack of the disease, identifying whether a disease or disorder is associated with the contact activation system, and/or for research purposes, including, e.g., studying the mechanism of a disease and/or biological pathways/processes involved in the disease, which may be relied upon for the development of new therapies.

Contact Activation System Metabolite Biomarkers

The methods and kits described herein are based, at least in part, on the identification of metabolites that were found to be differentially present in samples from subjects having HAE as compared with samples from healthy subjects, and/or differentially present in samples at different stages of such a disease (e.g., basal versus attack). As used herein, the term "metabolite biomarker" or "metabolite biomarker set" refers to a metabolite or set of metabolites that are present at different levels in samples from different groups of subjects, for example, subjects having a disease associated with the contact system versus healthy subjects (e.g., subjects who are free of the disease), or subjects having the disease and being at the quiescence stage versus subjects under the attack of the disease. Such biomarker/biomarker sets may be used in both diagnostic/prognostic applications and non-clinical applications (e.g., for research purposes).

In some embodiments, a metabolite biomarker may be present at an elevated level in samples from subjects having a disease associated with the contact activation system (e.g., HAE) as compared to the level of the same metabolite biomarker in samples from healthy subjects. In some embodiments, a metabolite biomarker may be present at a reduced level in samples from subjects having a disease associated with the contact activation system (e.g., HAE) as compared to the level of the biomarker in samples from healthy subjects. In yet other instances, a metabolite biomarker may be present at an elevated level in samples obtained from subjects under attack of a disease as described herein as compared with subjects during disease quiescence. Alternatively, a metabolite biomarker may be present at a reduced level in samples obtained from subjects under attack of a disease as described herein as compared with subjects during disease quiescence.

In some embodiments, a metabolite biomarker set containing one or more biomarkers can be analyzed in the methods described herein. When the metabolite biomarker set contains more than one biomarker, all of the biomarkers may present at elevated levels or reduced levels in subjects having a disease as compared with health subjects. Alternatively, a metabolite biomarker set may contain at least one biomarker that is elevated in subjects having the disease as compared with healthy subjects and at least one biomarker that is reduced in subjects having the disease as compared with healthy subjects.

Similarly, a metabolic biomarker set for differentiating subjects under attack of a disease from subjects in disease quiescence, the biomarker set may contain multiple biomarkers that are all elevated or reduced in a first disease stage (e.g., attack) as compared with a second disease stage (e.g., quiescence). Alternatively, the biomarker set may contain at least one biomarker that is elevated in the first disease stage as compared with the second disease stage and at least one biomarker that is reduced in the first disease stage as compared with the second disease stage.

Table 1 below provides metabolite biomarkers that can be evaluated by the methods described herein to evaluate subjects or biological samples from subjects for diseases associated with the contact activation system.

TABLE 1

Contact System Activation Biomarkers

| Metabolism Pathways | Metabolite Biomarker |
|---|---|
| Serotonin production | Serotonin |
| | Tryptophan |
| | Indolelactate |
| | Indolepropionate |
| Antioxidant | Gamma-/beta-tocopherol |
| | Ascorbate |
| Fatty acid amide hydrolase activity | Palmitic amide |
| | Oleamide |
| | Linoleamide |
| Lipid peroxide biomarkers | 9-hydroxyoctadecadienoic acid (9-HODE) |
| | 13-hydroxyoctadecadienoic acid (13-HODE) |
| | 9,10-di-hdroxy-12Z-octadecenoic acid (9,10-DiHOME) |
| | 12,13-dihydroxy-9Z-octadecenoic acid (12,13-DiHOME) |
| | 19,20-dihydroxy-4Z,7Z,10Z,13Z,16Z-docosapentaenoic acid (19,20 DiHDPA). |
| Sulfur metabolism | N-acetylmethionin |
| | Methionine sulfone |
| | S-adenosylhomocysteine |
| | Cysteine |
| | Cysteine sulfinic acid |
| Steroid metabolism | Pregnenolone sulfate |
| | 5alpha-pregnan-3beta,20beta-diol monosulfate |
| | Pregnen-diol disulfate; pregn steroid monosulfate |
| | Prenanediol-3-glucuronide |
| | Cortisol |
| | Corticosterone* |
| | Cortisone |
| | Dehydroisoandrosterone sulfate (DHEA-S) |
| | 16a-hydroxy DHEA 3-sulfate |
| | Epiandrosterone sulfate |
| | Androsterone sulfate |
| | 4-androsten-3beta, 17beta-diol monosulfate |
| | 4-androsten-3alpha, 17alpha-diol monosulfate |
| | 4-androsten-3beta, 17beta-diol disulfate |
| | 5alpha-androstan-3alpha,17alpha-diol monosulfate |
| | 5alpha-androstan-3beta,17-beta-diol disulfate |
| | Andro steroid monosulfate |
| | Etiocholanolone glucuronide |
| | Pregnanolone/alloprenanolone sulfate |
| Fatty acids | Eicosapentaenoate* |
| | Mead acid* |
| | Stearidonate* |
| Cofactor precursors | Nicotinamide* |
| | Pantothenate* |

*Indicates metabolites that were identified as being differentially present in samples from HAE patients during an attack as compared to HAE patients during quiescence.

In some embodiments, the biomarker set to be measured and analyzed in any of the methods described herein includes at least one (e.g., 1, 2, 3, 4, 5, 6, 7, 8, 9, 10, or more) metabolites selected from Table 1.

As described in Example 1, it was unexpectedly found that several metabolites involved in different cellular processes and pathways were differentially present in samples from subjects having HAE as compared to healthy subjects. This data indicates that the metabolites or metabolite pathways shown in Table 1 may play a role in or be affected by diseases associated with the contact system.

The metabolite biomarkers described herein may be characterized as "involved in" or "associated with" a particular pathway or activity. As used herein, the terms "involved in" or "associated with" refer to a metabolite that contributes to pathway. For example, a metabolite that is involved in or associated with a pathway may perform a function within the pathway, be a precursor of another molecule in a pathway, a substrate for an enzyme in a pathway) or be a product, including a byproduct or a production of degradation or a molecule, of a pathway. In some embodiments, the pathway is a metabolic pathway, such as a biosynthetic pathway or catabolic pathway. In some embodiments, a metabolite may be described as associated with the activity of a particular enzyme. For example, a metabolite associated with activity of an enzyme may be a substrate of the enzyme, a product of the activity of the enzyme, or a cofactor that presence of which regulates or promotes activity of the enzyme. In some embodiments, the level of a substrate of an enzyme or a product of an enzyme is an indication of the level of activity of the enzyme (e.g., during the disease or a particular state of the disease).

As used herein, the term "precursor," such as a cofactor precursor, refers to a metabolite that precedes another molecule (e.g., a product) in a synthetic pathway. For example, a cofactor precursor is a metabolite that is in the synthetic pathway of the cofactor and may be modified or otherwise used to produce the cofactor. As also used herein, the term "cofactor" refers to a molecule that interacts with an enzyme, thereby promoting the activity of the enzyme.

In some embodiments, the biomarker set includes serotonin or one or more metabolites that is involved in serotonin production, e.g., one or more metabolite that is involved in serotonin production selected from Table 1.

In some embodiments, the biomarker set includes one or more metabolites associated with fatty acid amide hydrolase activity, e.g., one or more metabolites that are involved in serotonin production selected from Table 1. Metabolites associated with fatty acid amide hydrolase activity can be any metabolite that is involved in a reaction catalyzed by fatty acid amide hydrolase. Such a metabolite may be a substrate of the enzyme, a product of the enzyme, or any intermediate thereof.

In some embodiments, the biomarker set includes one or more metabolite that is a lipid peroxide, which refers to any product of the reaction of lipid peroxidation. Examples include the lipid peroxide compounds listed in Table 1. In some embodiments, the biomarker set includes one or more metabolites associated sulfur metabolism, e.g., one or more metabolite that is involved in sulfur metabolism selected from Table 1.

In some embodiments, the biomarker set includes one or more metabolite associated with steroid metabolism, e.g., one or more metabolite that is involved in steroid metabolism selected from Table 1.

As also described in Example 1, it was also found that several metabolites were differentially present in samples from subjects having HAE during an HAE attack as compared to subjects having HAE during quiescence (basal). In some embodiments, the biomarker set includes one or more metabolite that is a fatty acid, e.g., one or more metabolite that is a fatty acid selected from Table 1. In some embodiments, the biomarker set includes one or more metabolite that is a cofactor precursor, e.g., one or more metabolite that is a cofactor precursor selected from Table 1. In some embodiments, the biomarker set includes corticosterone.

Utilities of the Metabolite Biomarkers

One aspect of the present disclosure relates to methods for analyzing samples obtained from subjects (e.g., human patients) having, suspected of having, or being at risk for a disease associated with the contact activation system by measuring the level of a biomarker set as described herein in the sample. Results obtained from such assay methods would be useful for diagnostic and/or prognostic purposes, as well as for other non-clinical purposes, such as research purposes.

(i) Analysis of Biological Samples

The methods described herein involved providing a biological sample obtained from a subject. As used herein, a "biological sample" refers to a composition that comprises tissue, e.g., blood, plasma, or protein, from a subject. A sample includes both an initial unprocessed sample taken from a subject as well as subsequently processed, e.g., partially purified or preserved forms. Exemplary samples include blood, plasma, tears, or mucus. In some embodiments, the sample is a body fluid sample such as a serum or plasma sample. In some embodiments, multiple (e.g., at least 2, 3, 4, 5, or more) biological samples may be collected from subject, over time or at particular time intervals, for example to assess the disease progression or evaluate the efficacy of a treatment.

A biological sample can be obtained from a subject using any means known in the art. In some embodiments, the sample is obtained from the subject by collecting the sample (e.g., a blood sample) into an evacuated collection tube (e.g., an evacuated blood collection tube). In some embodiments, the evacuated collection tube contains one or more protease inhibitors, for example, to reduce or prevent ex vivo activation of the contact system during sample collection. Such protease inhibitors may be contained in a liquid formulation. In some embodiments, the protease inhibitors comprise at least one serine protease inhibitor and at least one cysteine protease inhibitor. Such evacuated collection tubes are known in the art. See, for example, PCT Application No. US2016/046681. Optionally, an evacuated blood collection tube may further comprise one or more anti-coagulants.

The terms "patient," "subject," or "individual" may be used interchangeably and refer to a subject who needs the analysis as described herein. In some embodiments, the subject is a human or a non-human mammal. In some embodiments, a subject is suspected of or is at risk for a disease or disorder associated with the contact activation system (e.g., HAE). Such a subject may exhibit one or more symptoms associated with the disease. Alternatively or in addition, such a subject may carry one or more risk factors for the disease, for example, a genetic factor associated with the disease (e.g., a genetic defect in CI-INH).

Alternatively, the subject who needs the analysis described herein may be a patient of the disease. Such a subject may be under the attack of the disease currently, or may suffer from the disease in the past (e.g., during disease quiescence currently). In some examples, the subject is a human patient who may be on a treatment of the disease, for example, a treatment involving a C1 esterase inhibitor (C1-INH), a plasma kallikrein inhibitor, or a bradykinin inhibitor. In other instances, such a human patient may be free of such a treatment.

Examples of diseases associated with the contact activation system include, without limitation, kallikrein-mediated disorders, e.g., a bradykinin-mediated disorder, such as hereditary angioedema (HAE), non-histamine-dependent idiopathic angioedema, rheumatoid arthritis, Crohn's disease, lupus, Alzheimer's disease, septic shock, burn injury, brain ischemia/reperfusion injury, cerebral edema, diabetic retinopathy, diabetic nephropathy, macular edema, vasculitis, arterial or venous thrombosis, thrombosis associated with ventricular assist devices or stents, heparin-induced thrombocytopenia with thrombosis, thromboembolic disease, and coronary heart disease with unstable angina pectoris, edema, eye disease, gout, intestinal bowel disease, oral mucositis, neuropathic pain, inflammatory pain, spinal stenosis-degenerative spine disease, post-operative ileus, aortic aneurysm, osteoarthritis, hereditary angioedema, pulmonary embolism, stroke, head trauma or peri-tumor brain edema, sepsis, acute middle cerebral artery (MCA) ischemic event (stroke), restenosis (e.g., after angioplasty), systemic lupus erythematosis nephritis, an autoimmune disease, an inflammatory disease, a cardiovascular disease, a neurological disease, a disease associated with protein misfolding, a disease associated with angiogenesis, hypertensive nephropathy and diabetic nephropathy, allergic and respiratory diseases (e.g., anaphylaxis, asthma, chronic obstructive pulmonary disease, acute respiratory distress syndrome, cystic fibrosis, persistent, rhinitis), and tissue injuries (e.g., burn or chemical injury).

In some embodiments, the disease or condition that is associated with the contact activation system is hereditary angioedema (HAE). Hereditary angioedema (HAE) is also known as "Quincke edema," C1 esterase inhibitor deficiency, C1 inhibitor deficiency, and hereditary angioneurotic edema (HANE). HAE is characterized by recurrent episodes of severe swelling (angioedema), which can affect, e.g., the limbs, face, genitals, gastrointestinal tract, and airway. Symptoms of HAE include, e.g., swelling in the arms, legs, lips, eyes, tongue, and/or throat; airway blockage that can involve throat swelling and sudden hoarseness; repeat episodes of abdominal cramping without obvious cause; and/or swelling of the intestines, which can be severe and can lead to abdominal cramping, vomiting, dehydration, diarrhea, pain, and/or shock. About one-third of individuals with HAE develop a non-itchy rash called erythema marginatum during an attack.

Swelling of the airway can be life threatening and causes death in some patients. Mortality rates are estimated at 15-33%. HAE leads to about 15,000-30,000 emergency department visits per year. Trauma or stress, e.g., dental procedures, sickness (e.g., viral illnesses such as colds and the flu), menstruation, and surgery can trigger an attack of angioedema. To prevent acute attacks of HAE, patients can attempt to avoid specific stimuli that have previously caused attacks. However, in many cases, an attack occurs without a known trigger. Typically, HAE symptoms first appear in childhood and worsen during puberty. On average, untreated individuals have an attack every 1 to 2 weeks, and most episodes last for about 3 to 4 days (ghr.nlm.nih.gov/condition/hereditary-angioedema). The frequency and duration of attacks vary greatly among people with hereditary angioedema, even among people in the same family.

There are three types of HAE, known as types I, II, and III. It is estimated that HAE affects 1 in 50,000 people, that type I accounts for about 85 percent of cases, type II accounts for about 15 percent of cases, and type III is very rare. Type III is the most newly described form and was originally thought to occur only in women, but families with affected males have been identified.

HAE is inherited in an autosomal dominant pattern, such that an affected person can inherit the mutation from one affected parent. New mutations in the gene can also occur, and thus HAE can also occur in people with no history of the disorder in their family. It is estimated that 20-25% of cases result from a new spontaneous mutation.

Mutations in the SERPING1 gene cause hereditary angioedema type I and type II. The SERPING1 gene provides instructions for making the C1 inhibitor protein, which is important for controlling inflammation. C1 inhibitor blocks the activity of certain proteins that promote inflammation. Mutations that cause hereditary angioedema type I lead to reduced levels of C1 inhibitor in the blood. In contrast, mutations that cause type II result in the production of a C1 inhibitor that functions abnormally. Without the proper levels of functional C1 inhibitor, excessive amounts of bradykinin are generated. Bradykinin promotes inflammation by increasing the leakage of fluid through the walls of blood vessels into body tissues. Excessive accumulation of fluids in body tissues causes the episodes of swelling seen in individuals with hereditary angioedema type I and type II.

Mutations in the F12 gene are associated with some cases of hereditary angioedema type III. The F12 gene provides instructions for making coagulation factor XII. In addition to playing a critical role in blood clotting (coagulation), factor XII is also an important stimulator of inflammation and is involved in the production of bradykinin. Certain mutations in the F12 gene result in the production of factor XII with increased activity. As a result, more bradykinin is generated and blood vessel walls become more leaky, which leads to episodes of swelling. The cause of other cases of hereditary angioedema type III remains unknown. Mutations in one or more as-yet unidentified genes may be responsible for the disorder in these cases.

HAE can present similarly to other forms of angioedema resulting from allergies or other medical conditions, but it differs significantly in cause and treatment. When HAE is misdiagnosed as an allergy, it is most commonly treated with antihistamines, steroids, and/or epinephrine, which are typically ineffective in HAE, although epinephrine can be used for life-threatening reactions. Misdiagnoses have also resulted in unnecessary exploratory surgery for patients with abdominal swelling, and in some HAE patients abdominal pain has been incorrectly diagnosed as psychosomatic.

C1 inhibitor therapies, as well as other therapies for HAE, are described in Kaplan, A. P., *J Allergy Clin Immunol*, 2010, 126(5):918-925.

Acute treatment of HAE attacks is provided to halt progression of the edema as quickly as possible. C1 inhibitor concentrate from donor blood, which is administered intravenously, is one acute treatment; however, this treatment is not available in many countries. In emergency situations where C1 inhibitor concentrate is not available, fresh frozen plasma (FFP) can be used as an alternative, as it also contains C1 inhibitor.

Purified C1 inhibitor, derived from human blood, has been used in Europe since 1979. Several C1 inhibitor treatments are now available in the U.S. and two C1 inhibitor products are now available in Canada. Berinert (CSL Behring), which is pasteurized, was approved by the F.D.A. in 2009 for acute attacks. CINRYZE®, which is nanofiltered, was approved by the F.D.A. in 2008 for prophylaxis. Rhucin/Ruconest (Pharming) is a recombinant C1 inhibitor under development that does not carry the risk of infectious disease transmission due to human blood-borne pathogens.

Treatment of an acute HAE attack also can include medications for pain relief and/or IV fluids.

Other treatment modalities can stimulate the synthesis of C1 inhibitor, or reduce C1 inhibitor consumption. Androgen medications, such as danazol, can reduce the frequency and severity of attacks by stimulating production of C1 inhibitor.

*Helicobacter pylori* can trigger abdominal attacks. Antibiotics to treat *H. pylori* will decrease abdominal attacks.

Newer treatments attack the contact cascade. Ecallantide (KALBITOR®) inhibits plasma kallikrein and has been approved in the U.S. Icatibant (FIRAZYR®, Shire) inhibits the bradykinin B2 receptor, and has been approved in Europe and the U.S.

Diagnosis of HAE can rely on, e.g., family history and/or blood tests. Laboratory findings associated with HAE types I, II, and III are described, e.g., in Kaplan, A. P., *J Allergy Clin Immunol,* 2010, 126(5):918-925. In type I HAE, the level of C1 inhibitor is decreased, as is the level of C4, whereas C1q level is normal. In type II HAE, the level of C1 inhibitor is normal or increased; however, C1 inhibitor function is abnormal. C4 level is decreased and C1q level is normal. In type III, the levels of C1 inhibitor, C4, and C1q can all be normal. The present disclosure is based, at least in part, on the identification of metabolites that have differential levels in samples from HAE patients as compared to healthy individuals (Table 1). Measuring the levels of biomarker sets of these metabolites can be used to identify whether a subject has a disease, such as HAE. In some embodiments, the methods may be used to determine whether a patient has had or is having an HAE attack.

Symptoms of HAE can be assessed, for example, using questionnaires, e.g., questionnaires that are completed by patients, clinicians, or family members. Such questionnaires are known in the art and include, for example, visual analog scales. See, e.g., McMillan, C. V. et al. *Patient.* 2012; 5(2):113-26.

The biological sample described herein can be subject to analysis by measuring the level of a biomarker set as described herein in the biological sample. Levels (e.g., the amount) of a biomarker disclosed herein, or changes in levels the biomarker, can be assessed using assays described herein and/or assays known in the art. One or more of the biomarkers described herein may be analyzed using convention methods. In some embodiments, the level of a biomarker is assessed or measured by directly detecting the metabolite in a biological sample. Alternatively or in addition, the level of a metabolite can be assessed or measured by indirectly in a biological sample, for example, by detecting the level of a binding agent that binds to the metabolite (e.g. an antibody in an immunoassay) or by detecting an activity of the metabolite.

The type of detection assay used for the detection and/or quantification of a contact activation system biomarker such as those provided herein will depend on the particular situation in which the assay is to be used (e.g., clinical or research applications), and on the kind and number of biomarkers to be detected, and on the kind and number of patient samples to be run in parallel, to name a few parameters.

In some embodiments, the biomarker is measured using mass spectrometry. In general, mass spectrometry relies on separating ions of a molecule based on the mass to charge ratio of the ion. In some embodiments, the mass spectrometry is tandem mass spectrometry in which involves more than one round of mass spectroscopy. The levels of metabolites may be measured by comparing the mass spectrum obtained from the mass spectrometry for the sample to the mass spectrum of another sample or a reference or control sample. The identity of the metabolites in the spectra may be ascertained by comparing a spectrum to a library of spectra or a spectrum of a known metabolite. In some embodiments, components of the biological sample may be separated, for example using chromatographic methods as described herein, prior to detecting the metabolite biomarker. Examples of separation methods include, for example, gas chromatography, liquid chromatography, capillary electrophoresis, and ion mobility. In some embodiments, the biomarker is measured using liquid chromatography followed by mass spectrometry.

In some embodiments, the biomarker is measured using a chromatographic methods. Chromatography allows for separation of molecules (in a mobile phase) based on movement of the molecules through a medium (a solid phase). Examples of chromatographic methods that may be compatible with the methods described herein include, without limitation, gas chromatography, liquid chromatography, reverse-phase chromatography, ion exchange chromatography, size exclusion chromatography, and affinity chromatography.

In some embodiments, the biomarker is measured using an immunoassay. Examples of immunoassays include, without limitation immunoblotting assays (Western blots), enzyme linked immunosorbent assays (ELISAs) (e.g., sandwich ELISAs), radioimmunoassays, electrochemiluminescence-based detection assays, magnetic immunoassays, lateral flow assays, and related techniques. Additional suitable immunoassays for detecting a biomarker provided herein will be apparent to those of skill in the art. It will be apparent to those of skill in the art that this disclosure is not limited to immunoassays, however, and that detection assays that rely on a chromogenic substrate can also be useful for the detection and/or quantification of contact system biomarkers as provided herein.

ELISAs are known in the art (see, e.g., Crowther, John R (2009). "The ELISA Guidebook." 2nd ed. Humana Press and Lequin R (2005). "Enzyme immunoassay (EIA)/enzyme-linked immunosorbent assay (ELISA)". *Clin. Chem.* 51 (12): 2415-8) and exemplary ELISAs are described herein. Kits for performing ELISAs are also known in the art and commercially available (see, e.g., ELISA kits from Life Technologies and BD Biosciences).

In some embodiments, an immunoassay is used to measure levels of the metabolite biomarker(s). The immunoassays described herein may be in the format of a sandwich ELISA, in which a first binding agent that specifically binds a metabolite of the biomarker set is immobilized on a support member. The support member can then be incubated with a biological sample as described herein for a suitable period of time under conditions that allow for the formation of complex between the binding agent and the metabolite in the sample. Such a complex can then be detected using a detection agent that binds the metabolite, the binding agent-metabolite complex, or the binding agent. The detection agent can be conjugated to a label, which can release a signal directly or indirectly. The intensity of the signal represents the level of the metabolite in the sample. In some embodiments, the detection agent is detected and its level represents the level of the metabolite in the sample.

Any binding agent that specifically binds to a desired metabolite may be used in the methods and kits described herein to measure the level of a metabolite in a biological sample. In some embodiments, the binding agent is an antibody that specifically binds to a desired metabolite. In some embodiments, the binding agent is an aptamer antibody that specifically binds to a desired metabolite. In some embodiments, a sample may be contacted, simultaneously or sequentially, with more than one binding agent that bind different metabolites (e.g., multiplexed analysis, for example the SOMAScan™ assay (SOMALogic)). The biological sample is contacted with a binding agent under appropriate conditions. In general, the term "contact" refers to an exposure of the binding agent with the biological sample or agent for a suitable period sufficient for the formation of complexes between the agent and the metabolite in the sample, if any. In some embodiments, the contacting is performed by capillary action in which a biological sample or agent is moved across a surface of the support membrane.

In some embodiments, the immunoassays may be performed on low-throughput platforms, including in single immunoassay format. For example, a low throughput platform may be used to measure the presence and amount of a metabolite in biological samples (e.g., biological tissues, tissue extracts) for diagnostic methods, monitoring of disease and/or treatment progression, and/or predicting whether a disease or disorder may benefit from a particular treatment.

In some embodiments, it may be necessary to immobilize a binding agent to the support member. Methods for immobilizing a binding agent will depend on factors such as the nature of the binding agent and the material of the support member and may require particular buffers. Such methods will be evident to one of ordinary skill in the art. For example, the biomarker set in a biological sample as described herein may be measured using any of the kits and/or detecting devices which are also described herein.

In some embodiments, the biomarker is measured with an enzyme-coupled assay. For example, the biomarker present in a biological sample may be used as the substrate of an enzymatic reaction, which may be coupled to a second reaction. Such a reaction results in the generation of a product (e.g., a cofactor) that can be detected, for example by a change in absorbance or fluorescence.

As used herein, the terms "measuring" or "measurement," or alternatively "detecting" or "detection," mean assessing the presence, absence, quantity or amount (which can be an effective amount) of a substance within a sample, including the derivation of qualitative or quantitative concentration levels of such substances, or otherwise evaluating the values or categorization of a subject.

Assays, e.g., Western blot assays, may further involve use of a quantitative imaging system, e.g., LICOR imaging technology, which is commercially available (see, e.g., the Odyssey® CLx infrared imaging system from LI-COR Biosciences). In some embodiments, an electrochemiluminescence detection assay or an assay relying on a combination of electrochemiluminescence and patterned array technology is used (e.g., an ECL or MULTI-ARRAY technology assay from Meso Scale Discovery (MSD)).

In any of the methods described herein, the level of a metabolite of a biomarker set can be compared to the level of the metabolite in a control sample or a reference sample.

The methods and kits described herein, involving any of the metabolite biomarker set also described herein, can be applied for the evaluation of a disease associated with the contact activation system, such as those described herein.

(ii) Diagnostic and/or Prognostic Applications

The levels of metabolites presented in Table 1 detected in samples from subjects can be used as reliable biomarkers for diagnosing diseases associated with the contact activation system (e.g., HAE), monitoring the progress of such a disease, assessing the efficacy of a treatment for the disease, identifying patients suitable for a particular treatment, and/or predicting disease attack in a subject.

Accordingly, described herein are diagnostic and prognostic methods for a disease associated with the contact activation system based on the level of a biomarker set in a biological sample obtained from a subject. In some embodiments, the level of the biomarker, as measured using any of the methods described herein, can be relied on to evaluate whether a subject (e.g., a human patient) from whom the biological sample is obtained, has or is at risk for a disease associated with the contact activation system, such as a disease associated with plasma kallikrein, e.g., HAE or autoimmune disease such as RA, UC, and Crohn's disease.

In some embodiments, the level of the biomarker can then be compared with a reference sample or a control sample to determine a value indicating the amount of the metabolite in the sample. In some embodiments, a value for a biomarker is obtained by comparing the level of a metabolite in a sample to the level of another metabolite (e.g., an internal control or internal standard) in the sample. Such a biomarker value may be a normalized value over the internal control or internal standard. The value of the biomarker can be compared to a reference value to determine whether the subject has or is at risk for the disease associated with the contact system. The reference value may represent the level of the corresponding biomarker in subjects (e.g., human subjects) free of the target disease. In some embodiments, if the level or value of the biomarker is higher than a reference level or value, the subject can be identified as having or at risk for a disease associated with the contact activation system. In some embodiments, if the level or value of the biomarker is lower than a reference level or value, the subject can be identified as having or at risk for a disease associated with the contact activation system.

In some embodiments, the level of the biomarker can be compared to a predetermined threshold for the metabolite, a deviation from which may indicate the subject has a disease associated with the contact system. The predetermined threshold may represent the value of the biomarker that distinguishes the level of the biomarker in patients having the target disease from the level of the biomarker in patients free of the target disease.

In some embodiments, the biomarker set includes more than one metabolites that are differentially present (elevated and/or reduced) in a subject having or being at risk of having the disease as relative to healthy individuals. In some examples, the biomarker set includes at least one metabolite biomarker that has an elevated level in a subject having or being at risk of having the disease and at least one metabolite biomarkers that has a reduced level in the subject having or at risk for the disease. In some embodiments, the biomarker set includes more than one metabolite biomarkers that have elevated levels in a subject having or being at risk of having the disease as relative to those in healthy controls. In other embodiments, the biomarker set includes more than one metabolite biomarkers that have reduced levels in a subject having or being at risk of having the disease as relative to those in healthy controls.

In some embodiments, the control sample or reference sample is a biological sample obtained from a healthy individual. In some embodiments, the control sample or reference sample contains a known amount of the metabolite to be assessed.

As used herein, a control sample may be a healthy subject or healthy individual, that is apparently free of the target disease (e.g., a disease associated with the contact system) at the time the level of the metabolite(s) is measured or has no history of the disease.

The term "control subject" encompasses an individual subject or a group of subjects having similar characteristics, for example a group of healthy individuals having certain features matching those of the candidate subject, e.g., age, gender, ethnic group, etc. In some embodiments, the level of a biomarker in a control subject is used to establish a reference value (e.g., the average level of the biomarker in a control subject, which includes a group of subjects) that may be compared to the level of the biomarker in the candidate or test subject.

The control level refers to the level of a metabolite biomarker set as described herein in a control subject. The control level can be a predetermined level or threshold. Such a predetermined level can represent the level of the metabolite in a population of subjects that do not have or are not at risk for the target disease (e.g., the average level in the population of healthy subjects). It can also represent the level of the metabolite in a population of subjects that have the target disease.

The predetermined level can take a variety of forms. For example, it can be single cut-off value, such as a median or mean. In some embodiments, such a predetermined level can be established based upon comparative groups, such as where one defined group is known to have a target disease and another defined group is known to not have the target disease. Alternatively, the predetermined level can be a range, for example, a range representing the levels of the metabolite in a control population.

The control level as described herein can be determined by routine technology. In some examples, the control level can be obtained by performing a conventional method (e.g., the same assay for obtaining the level of the metabolite in a test sample as described herein) on a control sample as also described herein. In other examples, levels of the metabolite can be obtained from members of a control population and the results can be analyzed by, e.g., a computational program, to obtain the control level (a predetermined level) that represents the level of the metabolite in the control population.

By comparing the level of a biomarker in a sample obtained from a candidate subject to the reference value as described herein, it can be determined as to whether the candidate subject has or is at risk for a disease associated with the contact system (e.g., HAE). For example, if the level of biomarker(s) in a sample of the candidate subject deviates from the reference value (e.g., increased as compared to the reference value), the candidate subject might be identified as having or at risk for the disease. When the reference value represents the value range of the level of the biomarker in a population of subjects that have the target disease, the value of biomarker in a sample of a candidate falling in the range indicates that the candidate subject has or is at risk for the target disease.

As used herein, "an elevated level" or "a level above a reference value" means that the level of the biomarker is higher than a reference value, such as a pre-determined threshold of a level the biomarker in a control sample. Control levels are described in detail herein. An elevated level of a biomarker includes a level of the biomarker that is, for example, 1%, 5%, 10%, 20%, 30%, 40%, 50%, 60%, 70%, 80%, 90%, 100%, 150%, 200%, 300%, 400%, 500% or more above a reference value. In some embodiments, the level of the biomarker in the test sample is at least 1.1, 1.2, 1.3, 1.4, 15, 1.6, 1.7, 1.8, 1.9, 2, 2.5, 3, 3.5, 4, 4.5, 5, 5, 6, 7, 8, 9, 10, 50, 100, 150, 200, 300, 400, 500, 1000, 10000-fold or higher than the level of the biomarker in a reference sample.

As used herein, "a decreased level" or "a level below a reference value" means that the level of the biomarker is lower than a reference value, such as a pre-determined threshold of the biomarker in a control sample. Control levels are described in detail herein. A decreased level of the biomarker includes a level of the biomarker that is, for example, 1%, 5%, 10%, 20%, 30%, 40%, 50%, 60%, 70%, 80%, 90%, 100%, 150%, 200%, 300%, 400%, 500% or more lower than a reference value. In some embodiments, the level of the biomarker in the test sample is at least 1.1, 1.2, 1.3, 1.4, 15, 1.6, 1.7, 1.8, 1.9, 2, 2.5, 3, 3.5, 4, 4.5, 5, 5, 6, 7, 8, 9, 10, 50, 100, 150, 200, 300, 400, 500, 1000, 10000-fold or lower than the level of the biomarker in a reference sample.

In some embodiments, the candidate subject is a human patient having a symptom of a disease associated with the contact activation system, such as a pKal-mediated disorder, e.g., HAE or an autoimmune disease such as RA, UC, and Crohn's disease. For example, the subject has edema, swelling wherein said swelling is completely or predominantly peripheral; hives; redness, pain, and swelling in the absence of evidence of infection; non-histamine-mediated edema, recurrent attacks of swelling, or a combination thereof. In other embodiments, the subject has no symptom of a pKal-mediated disorder at the time the sample is collected, has no history of a symptom of a pKal-mediated disorder, or no history of a pKal-mediated disorder such as HAE. In yet other embodiments, the subject is resistant to an antihistamine therapy, a corticosteroid therapy, or both.

A subject identified in the methods described herein may be subject to a suitable treatment, such as treatment with a pKal inhibitor, as described herein.

The assay methods and kits described herein also can be applied for evaluation of the efficacy of a treatment for a disease associated with the contact system, such as those described herein, given the correlation between the level of the biomarkers and such diseases. For examples, multiple biological samples (e.g., blood or plasma samples) can be collected from a subject to whom a treatment is performed either before and after the treatment or during the course of the treatment. The levels of a biomarker can be measured by any of the assay methods as described herein and values (e.g., amounts) of a biomarker can be determined accordingly. For example, if an elevated level of a biomarker indicates that a subject has a target disease and the level of the biomarker decreases after the treatment or over the course of the treatment (the level of the biomarker in a later collected sample as compared to that in an earlier collected sample), it indicates that the treatment is effective. As another example, if a reduced level of a biomarker indicates that a subject has a target disease and the level of the biomarker increases after the treatment or over the course of the treatment (the level of the biomarker in a later collected sample as compared to that in an earlier collected sample), it indicates that the treatment is effective. In some examples, the treatment involves an effective amount of a therapeutic agent, such as a plasma kallikrein inhibitor, a bradykinin B2 receptor antagonist, or a C1 esterase inhibitor (C1-INH). Examples of the therapeutic agents include, but not limited to, lanadelumab, ecallantide, icatibant, and human plasma-derived C1-INH.

If the subject is identified as not responsive to the treatment, a higher dose and/or frequency of dosage of the therapeutic agent are administered to the subject identified. In some embodiments, the dosage or frequency of dosage of the therapeutic agent is maintained, lowered, or ceased in a subject identified as responsive to the treatment or not in need of further treatment. Alternatively, a different treatment can be applied to the subject who is found as not responsive to the first treatment.

In other embodiments, the values of a biomarker or biomarker set can also be relied on to identify that a disorder is associated with the contact system or that the disorder may be treatable, for example by a pKal inhibitor. To practice this method, the level of a biomarker in a sample collected from a subject (e.g., a blood sample or a plasma sample) having a target disease can be measured by a suitable method, e.g., those described herein such as mass spectrometry, chromatography, immunoassays. If the level of the biomarker deviates from the reference value (e.g., elevated or decreased), it indicates that a pKal inhibitor may be effective in treating the disease. If the disease is identified as being susceptible (can be treated by) to a pKal inhibitor, the method can further comprise administering to the subject having the disease an effective amount of a pKal inhibitor, such as an anti-pKal antibody or an inhibitory peptide (e.g., lanadelumab, ecallantide, etc.); a bradykinin 2 receptor inhibitor (e.g., icatibant); and/or a C1-INH (e.g. human plasma-derived C1-INH).

Also within the scope of the present disclosure are methods of evaluating the severity of a disease associated with the contact system or the disease state. For example, as described herein, HAE may be in the quiescent state (basal state), during which the subject does not experience symptoms of the disease. HAE attacks are typically recurrent episodes in which the subject may experience pain and swelling, for example in the hands, feet, face, gastrointestinal tract, genitals, and larynx (throat) that can last from two to five days. In some embodiments, the level of one or more biomarker is indicative of whether the subject will experience, is experiencing, or will soon experience an HAE attack. In some embodiments, the methods involve comparing the level of a biomarker in a sample obtained from a subjecting having HAE to the level of the biomarker in a sample from the same subject, for example a sample obtained from the same subject at basal state or a sample obtained from the same subject during a HAE attack.

Other aspects of the disclosure provide methods for assessing the risk of disease attack (e.g., HAE attack). As described herein, HAE attacks are typically recurrent episodes during which the subject may experience symptoms such as pain and swelling. In some embodiments, the level of one or more biomarker is indicative of whether the subject is at risk of having an HAE attack. In some embodiments, the methods involve comparing the level of a biomarker in a sample obtained from a subjecting having HAE to the level of the biomarker in a sample from the same subject, for example a sample obtained from the same subject at basal state or a sample obtained from the same subject during a HAE attack. For example, an increase (or a decrease) in the level of a biomarker associated with an HAE attack as compared to the level of the biomarker in another sample from the subject may indicate that the subject is at risk of having an HAE attack.

In some embodiments, the methods involve comparing the level of a biomarker in a sample obtained from a subjecting having HAE to the level of the biomarker in a control or reference sample. In some embodiments, the level of the biomarker in the control or reference sample represents the level of the biomarker that indicates a HAE attack state. For example, a level of the biomarker in a sample obtained from a subjecting having HAE that is similar to the level of the biomarker in a reference that represents an HAE attack state, may indicate that the subject is at risk of having a HAE attack. In some embodiments, the level of the biomarker in the control or reference sample represents the level of the biomarker that indicates HAE in the basal state. For example, a level of the biomarker in a sample obtained from a subjecting having HAE that deviates (is elevated or reduced) to the level of the biomarker in a reference that represents a HAE in the basal state, may indicate that the subject is at risk of having a HAE attack.

(iii) Non-Clinical Applications

Further, levels of any of the biomarker set described herein may be used for research purposes. Although many diseases associated with the contact activation system have been identified, it is possible that other diseases are mediated by similar mechanisms or involve similar components. In some embodiments, the methods described herein may be used to identify a disease as being associated with the contact activation system or with components of the contact activation system. In some embodiments, the methods described herein may be used to study mechanisms (e.g., the discovery of novel biological pathways or processes involved in disease development) or progression of a disease.

In some embodiments, the levels of biomarker sets, as described herein, may be relied on in the development of new therapeutics for a disease associated with the contact activation system. For example, the levels of a biomarker set may be measured in samples obtained from a subject having been administered a new therapy (e.g., a clinical trial). In some embodiments, the level of the biomarker set may indicate the efficacy of the new therapeutic or the progression of the disease in the subject prior to, during, or after the new therapy.

Kits and Detecting Devices for Measuring Metabolite Biomarker Sets

The present disclosure also provides kits and detecting devices for use in measuring the level of a biomarker set as described herein. Such a kit or detecting device can comprise binding agents that specifically bind to metabolite biomarkers, such as those listed in Table 1. For example, such a kit or detecting device may comprise at least two binding agents that are specific to two different metabolite biomarkers selected from Table 1. In some instances, the kit or detecting device comprises binding agents specific to all members of the metabolite biomarker set described herein.

In some embodiments, one or more of the binding agents is an antibody that specifically binds to a metabolite of the biomarker set. In some embodiments, the one or more binding agents is an aptamer, such as a peptide aptamer or oligonucleotide aptamer, that specifically binds to a metabolite of the biomarker set.

In some embodiments, the kits further comprise a detection agent (e.g., an antibody binding to the binding agent) for detecting binding of the agent to the metabolite(s) of the biomarker set. The detection agent can be conjugated to a label. In some embodiments, the detection agent is an antibody that specifically binds to at least one of the binding agents. In some embodiments, the binding agent comprises a tag that can be identified and, directly or indirectly, bound by a detection agent.

In some embodiments, the kit or device further includes a support member. In some embodiments, the support member is a membrane, such as a nitrocellulose membrane, a polyvinylidene fluoride (PVDF) membrane, or a cellulose acetate membrane. In some examples, the immunoassay may be in a Western blot assay format or a lateral flow assay format.

In some embodiments, the support member is a multi-well plate, such as an ELISA plate. In some embodiments, the immunoassays described herein can be carried out on high throughput platforms. In some embodiments, multi-well plates, e.g., 24-, 48-, 96-, 384- or greater well plates, may be used for high throughput immunoassays. Individual immunoassays can be carried out in each well in parallel. Therefore, it is generally desirable to use a plate reader to measure multiple wells in parallel to increase assay throughput. In some embodiments, plate readers that are capable of imaging multi-wells (e.g., 4, 16, 24, 48, 96, 384, or greater wells) in parallel can be used for this platform. For example, a commercially available plate reader (e.g., the plate::vision system available from Perkin Elmer, Waltham, MA) may be used. This plate reader is capable of kinetic-based fluorescence analysis. The plate::vision system has high collection efficiency optics and has special optics designed for the analysis of 96 wells in parallel. Additional suitable parallel plate readers include but are not limited to the SAFIRE (Tecan, San Jose, CA), the FLIPRTETRA® (Molecular Devices, Union City, CA), the FDSS7000 (Hamamatsu, Bridgewater, NJ), and the CellLux (Perkin Elmer, Waltham, MA).

In the kit or detecting device, one or more of the binding agents may be immobilized on a support member, which can be a membrane, a bead, a slide, or a multi-well plate. Selection of an appropriate support member for the immunoassay will depend on various factor such as the number of samples and method of detecting the signal released from label conjugated to the second agent.

The kit can also comprise one or more buffers as described herein but not limited to a coating buffer, a blocking buffer, a wash buffer, and/or a stopping buffer.

In some embodiments, the kit can comprise instructions for use in accordance with any of the methods described herein. The included instructions can comprise a description of how to use the components contained in the kit for measuring the level of metabolites of a biomarker set in a biological sample collected from a subject, such as a human patient.

The instructions relating to the use of the kit generally include information as to the amount of each component and suitable conditions for performing the assay methods described herein. The components in the kits may be in unit doses, bulk packages (e.g., multi-dose packages), or sub-unit doses. Instructions supplied in the kits of the present disclosure are typically written instructions on a label or package insert (e.g., a paper sheet included in the kit), but machine-readable instructions (e.g., instructions carried on a magnetic or optical storage disk) are also acceptable.

The label or package insert indicates that the kit is used for evaluating the level of metabolites of a biomarker set. Instructions may be provided for practicing any of the methods described herein.

The kits of this present disclosure are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle).

Kits may optionally provide additional components such as interpretive information, such as a control and/or standard or reference sample. Normally, the kit comprises a container and a label or package insert(s) on or associated with the container. In some embodiments, the present disclosure provides articles of manufacture comprising contents of the kits described above.

Treatment of Diseases Associated with Contact Activation System

A subject at risk for or suffering from a disease associated with the contact activation system, as identified using the methods described herein, may be treated with any appropriate therapeutic agent. In some embodiments, provided methods include selecting a treatment for a subject based on the output of the described method, e.g., measuring the level of a biomarker set.

In some embodiments, the methods described herein provide methods of identifying a subject as a candidate for preventative (prophylactic) treatment. As used herein, a "preventative" treatment includes any therapy or treatment regimen that aims to prevent or reduce the incidence of a disease (e.g., HAE attack). In some embodiments, the methods further comprise administering a preventative treatment to the subject. Any of the therapeutic agents described herein (e.g., pKal inhibitors, such as lanadelumab). In some embodiments, the level of a metabolite biomarker set in a sample obtained from a subject indicates that the patient has or is at risk of having HAE (e.g., by comparing the level of the metabolite biomarker to the level in a reference or control sample). Any subject having or at risk of having HAE may be administered a prophylactic treatment. Selection of an appropriate therapeutic agent and administration regimen for a preventative treatment will be evident to one of ordinary skill in the art.

In some embodiments, the method comprises one or both of selecting or administering a therapeutic agent, e.g., a kallikrein inhibitor, a bradykinin B2 receptor inhibitor, and/or a C1 esterase inhibitor, for administration to the subject based on the output of the assay, e.g., biomarker detection.

In some embodiments, the therapeutic agent is administered one or more times to the subject. In some embodiments, a plasma kallikrein inhibitor is administered to a subject. In some embodiments, kallikrein inhibitor is a peptide, a small molecule inhibitor, a kallikrein antibody, or a fragment thereof. In some embodiments, an antagonist of bradykinin B2 receptor is administered to a subject. In some embodiments, a C1-INH is administered to a subject.

The therapeutic agent, e.g., kallikrein inhibitor, bradykinin B2 receptor inhibitor, and/or C1-INH, may be administered along with another therapy as part of a combination therapy for treatment of the disease or condition that involves the contact activation system. Combination therapy, e.g., with one or more of a kallikrein inhibitor, bradykinin B2 receptor antagonist, or C1-INH replacement agent, e.g., with one or more of a kallikrein inhibitor, bradykinin B2 receptor antagonist or C1-INH replacement agent and another therapy, may be provided in multiple different configurations. The first agent may be administered before or after the administration of the other therapy. In some situations, the first agent and another therapy (e.g., a therapeutic agent) are administered concurrently, or in close temporal proximity (e.g., a short time interval between the injections, such as during the same treatment session). The first agent and the other therapy may also be administered at greater temporal intervals.

Therapeutic Agents

Plasma kallikrein binding agents (e.g., binding proteins, e.g., polypeptides, e.g., inhibitory polypeptides, e.g., antibodies, e.g., inhibitory antibodies, or other binding agents, e.g., small molecules) are useful therapeutic agents for a variety of diseases and conditions, e.g., diseases and conditions that involve plasma kallikrein activity. For example, in some embodiments, the disease or condition that involves plasma kallikrein activity is hereditary angioedema (HAE).

In some embodiments a plasma kallikrein binding agent such as a plasma kallikrein inhibitor is administered to a subject at risk or suffering from a disease associated with the contact activation system.

A number of useful protein inhibitors of kallikrein, either tissue and/or plasma kallikrein, include a Kunitz domain. As used herein, a "Kunitz domain" is a polypeptide domain having at least 51 amino acids and containing at least two, and preferably three, disulfides. The domain is folded such that the first and sixth cysteines, the second and fourth, and the third and fifth cysteines form disulfide bonds (e.g., in a Kunitz domain having 58 amino acids, cysteines can be present at positions corresponding to amino acids 5, 14, 30, 38, 51, and 55, according to the number of the BPTI homologous sequences provided below, and disulfides can form between the cysteines at position 5 and 55, 14 and 38, and 30 and 51), or, if two disulfides are present, they can form between a corresponding subset of cysteines thereof. The spacing between respective cysteines can be within 7, 5, 4, 3, 2, 1 or 0 amino acids of the following spacing between positions corresponding to: 5 to 55, 14 to 38, and 30 to 51, according to the numbering of the BPTI sequence provided below. The BPTI sequence can be used as a reference to refer to specific positions in any generic Kunitz domain. Comparison of a Kunitz domain of interest to BPTI can be performed by identifying the best fit alignment in which the number of aligned cysteines in maximized.

The 3D structure (at high resolution) of the Kunitz domain of BPTI is known. One of the X-ray structures is deposited in the Brookhaven Protein Data Bank as "6PTI". The 3D structure of some BPTI homologues (Eigenbrot et al., *Protein Engineering* (1990) 3(7):591-598; Hynes et al., *Biochemistry* (1990) 29:10018-10022) are known. At least eighty one Kunitz domain sequences are known. Known human homologues include three Kunitz domains of LACI also known as tissue factor pathway inhibitor (TFPI) (Wun et al., *J. Biol. Chem.* (1988) 263(13):6001-6004; Girard et al., *Nature* (1989) 338:518-20; Novotny et al, *J. Biol. Chem.* (1989) 264(31):18832-18837) two Kunitz domains of Inter-α-Trypsin Inhibitor, APP-I (Kido et al. *J. Biol. Chem.* (1988) 263(34):18104-18107), a Kunitz domain from collagen, three Kunitz domains of TFPI-2 (Sprecher et al., *PNAS USA* (1994) 91:3353-3357), the Kunitz domains of hepatocyte growth factor activator inhibitor type 1, the Kunitz domains of Hepatocyte growth factor activator inhibitor type 2, the Kunitz domains described in U.S. Patent Publication No.: 2004-0152633. LACI is a human serum phosphoglycoprotein with a molecular weight of 39 kDa (amino acid sequence in Table 2) containing three Kunitz domains.

TABLE 2

Exemplary Natural Kunitz Domains

```
LACI          1 MIYTMKKVHA LWASVCLLLN LAPAPLNAds
(SEQ ID         eedeehtiit dtelpplklM
NO: 1)       51 HSFCAFKADD GPCKAIMKRF FFNIFTRQCE
                EFIYGGCEGN QNRFESLEEC
            101 KKMCTRDnan riikttlqqe kpdfCfleed
                pgiCrgyitr yfynnqtkqC
            151 erfkyggClg nmnnfetlee CkniCedgpn
                gfqvdnygtq inavnnsltp
            201 qstkvpslfe fhgpswCltp adrglCrane
                nrfyynsvig kCrpfkysqC
            251 ggnennftsk qeClraCkkg fiqriskggl
                iktkrkrkkqr vkiayeeif
            301 vknm
The signal sequence (1-28) is uppercase and
underscored
LACI-K1 (50-107) is uppercase
LACI-K2 (121-178) is underscored
LACI-K3 (211-270) is bold BPTI                 1          2          3          4          5
(SEQ ID  12345678901234567890123456789012345678901234567890012345678
NO: 2)   RPDFCLEPPYTGPCKARIIRYFYNAKAGLCQTFVYGGCRAKRNNFKSAEDCMRTCGGA
```

The Kunitz domains above are referred to as LACI-K1 (residues 50 to 107), LACI-K2 (residues 121 to 178), and LACI-K3 (213 to 270). The cDNA sequence of LACI is reported in Wun et al. (J. Biol. Chem. (1988) 263(13):6001-6004). Girard et al. (*Nature* (1989) 338:518-20) reports mutational studies in which the P1 residues of each of the three Kunitz domains were altered. LACI-K1 inhibits Factor VIIa (F.VIIa) when F.VIIa is complexed to tissue factor and LACI-K2 inhibits Factor Xa.

Proteins Containing Exemplary Kunitz Domains Include the Following, with SWISS-PROT Accession Numbers in Parentheses:

A4_HUMAN (P05067), A4_MACFA (P53601), A4_MACMU (P29216),
A4_MOUSE (P12023), A4_RAT (P08592), A4_SAISC (Q95241),
AMBP_PLEPL (P36992), APP2_HUMAN (Q06481), APP2_RAT (P15943),
AXP1_ANTAF (P81547), AXP2_ANTAF (P81548), BPT1_BOVIN (P00974),
BPT2_BOVIN (P04815), CA17_HUMAN (Q02388), CA36_CHICK (P15989),
CA36_HUMAN (P12111), CRPT_BOOMI (P81162), ELAC_MACEU (O62845),
ELAC_TRIVU (Q29143), EPPI_HUMAN (O95925), EPPI_MOUSE (Q9DA01),
HTIB_MANSE (P26227), IBP_CARCR (P00993), IBPC_BOVIN (P00976),
IBPI_TACTR (P16044), IBPS_BOVIN (P00975), ICS3_BOMMO (P07481),
IMAP_DROFU (P11424), IP52_ANESU (P10280), ISC1_BOMMO (P10831),
ISC2_BOMMO (P10832), ISH1_STOHE (P31713), ISH2_STOHE (P81129),

ISIK_HELPO (P00994), ISP2_GALME (P81906), IVB1_BUNFA (P25660),
IVB1_BUNMU (P00987), IVB1_VIPAA (P00991), IVB2_BUNMU (P00989),
IVB2_DABRU (P00990), IVB2_HEMHA (P00985), IVB2_NAJNI (P00986),
IVB3_VIPAA (P00992), IVBB_DENPO (P00983), IVBC_NAJNA (P19859),
IVBC_OPHHA (P82966), IVBE_DENPO (P00984), IVBI_DENAN (P00980),
IVBI_DENPO (P00979), IVBK_DENAN (P00982), IVBK_DENPO (P00981),
IVBT_ERIMA (P24541), IVBT_NAJNA (P20229), MCPI_MELCP (P82968),
SBPI_SARBU (P26228), SPT3_HUMAN (P49223), TKD1_BOVIN (Q28201),
TKD1_SHEEP (Q29428), TXCA_DENAN (P81658), UPTI_PIG (Q29100),
AMBP_BOVIN (P00978), AMBP_HUMAN (P02760), AMBP_MERUN (Q62577),
AMBP_MESAU (Q60559), AMBP_MOUSE (Q07456), AMBP_PIG (P04366),
AMBP_RAT (Q64240), IATR_HORSE (P04365), IATR_SHEEP (P13371),
SPT1_HUMAN (O43278), SPT1_MOUSE (Q9R097), SPT2_HUMAN (O43291),
SPT2_MOUSE (Q9WU03), TFP2_HUMAN (P48307), TFP2_MOUSE (O35536),
TFPI_HUMAN (P10646), TFPI_MACMU (Q28864), TFPI_MOUSE (O54819),
TFPI_RABIT (P19761), TFPI_RAT (Q02445), YN81_CAEEL (Q03610)

A variety of methods can be used to identify a Kunitz domain from a sequence database. For example, a known amino acid sequence of a Kunitz domain, a consensus sequence, or a motif (e.g., the ProSite Motif) can be searched against the GenBank sequence databases (National Center for Biotechnology Information, National Institutes of Health, Bethesda MD), e.g., using BLAST; against Pfam database of HMMs (Hidden Markov Models) (e.g., using default parameters for Pfam searching; against the SMART database; or against the ProDom database. For example, the Pfam Accession Number PF00014 of Pfam Release 9 provides numerous Kunitz domains and an HMM for identify Kunitz domains. A description of the Pfam database can be found in Sonhammer et al. *Proteins* (1997) 28(3):405-420 and a detailed description of HMMs can be found, for example, in Gribskov et al. *Meth. Enzymol.* (1990) 183:146-159; Gribskov et al. *Proc. Natl. Acad. Sci. USA* (1987) 84:4355-4358; Krogh et al. *J. Mol. Biol.* (1994) 235:1501-1531; and Stultz et al. *Protein Sci.* (1993) 2:305-314. The SMART database (Simple Modular Architecture Research Tool, EMBL, Heidelberg, DE) of HMMs as described in Schultz et al. *Proc. Natl. Acad. Sci. USA* (1998) 95:5857 and Schultz et al. *Nucl. Acids Res* (2000) 28:231. The SMART database contains domains identified by profiling with the hidden Markov models of the HMMer2 search program (R. Durbin et al. (1998) *Biological sequence analysis: probabilistic models of proteins and nucleic acids.* Cambridge University Press). The database also is annotated and monitored. The ProDom protein domain database consists of an automatic compilation of homologous domains (Corpet et al. *Nucl. Acids Res.* (1999) 27:263-267). Current versions of ProDom are built using recursive PSI-BLAST searches (Altschul et al. *Nucleic Acids Res.* (1997) 25:3389-3402; Gouzy et al. *Computers and Chemistry* (1999) 23:333-340) of the SWISS-PROT 38 and TREMBL protein databases. The database automatically generates a consensus sequence for each domain. Prosite lists the Kunitz domain as a motif and identifies proteins that include a Kunitz domain. See, e.g., Falquet et al. Nucleic Acids Res. (2002) 30:235-238.

Kunitz domains interact with target protease using, primarily, amino acids in two loop regions ("binding loops"). The first loop region is between about residues corresponding to amino acids 13-20 of BPTI. The second loop region is between about residues corresponding to amino acids 31-39 of BPTI. An exemplary library of Kunitz domains varies one or more amino acid positions in the first and/or second loop regions. Particularly useful positions to vary, when screening for Kunitz domains that interact with kallikrein or when selecting for improved affinity variants, include: positions 13, 15, 16, 17, 18, 19, 31, 32, 34, and 39 with respect to the sequence of BPTI. At least some of these positions are expected to be in close contact with the target protease. It is also useful to vary other positions, e.g., positions that are adjacent to the aforementioned positions in the three-dimensional structure.

The "framework region" of a Kunitz domain is defined as those residues that are a part of the Kunitz domain, but specifically excluding residues in the first and second binding loops regions, i.e., about residues corresponding to amino acids 13-20 of BPTI and 31-39 of BPTI. Conversely, residues that are not in the binding loop may tolerate a wider range of amino acid substitution (e.g., conservative and/or non-conservative substitutions).

In one embodiment, these Kunitz domains are variant forms of the looped structure including Kunitz domain 1 of human lipoprotein-associated coagulation inhibitor (LACI) protein. LACI contains three internal, well-defined, peptide loop structures that are paradigm Kunitz domains (Girard, T. et al., *Nature* (1989) 338:518-520). Variants of Kunitz domain 1 of LACI described herein have been screened, isolated and bind kallikrein with enhanced affinity and specificity (see, for example, U.S. Pat. Nos. 5,795,865 and 6,057,287). These methods can also be applied to other Kunitz domain frameworks to obtain other Kunitz domains that interact with kallikrein, e.g., plasma kallikrein. Useful modulators of kallikrein function typically bind and/or inhibit kallikrein, as determined using kallikrein binding and inhibition assays.

In some aspects, the plasma kallikrein inhibitor binds to the active form of plasma kallikrein. In some embodiments, the plasma kallikrein inhibitor, binds to and inhibits plasma kallikrein, e.g., human plasma kallikrein and/or murine kallikrein. Exemplary polypeptide plasma kallikrein agents are disclosed in U.S. Pat. Nos. 5,795,865, 5,994,125, 6,057, 287, 6,333,402, 7,628,983, and 8,283,321, 7,064,107, 7,276, 480, 7,851,442, 8,124,586, 7,811,991, and U.S. Publication No. 20110086801, the entire contents of each of which is incorporated herein by reference. In some embodiments, the plasma kallikrein inhibitor is an inhibitory polypeptide or peptide. In some embodiments, the inhibitory peptide is ecallantide (also referred to as DX-88 or KALBITOR®; SEQ ID NO: 3). In some embodiments, the kallikrein inhibitor comprises or consists of an about 58-amino acid sequence of amino acids 3-60 of SEQ ID NO:3 or the DX-88 polypeptide having the 60-amino acid sequence of SEQ ID NO:3.

Glu Ala Met His Ser Phe Cys Ala Phe Lys Ala Asp Asp Gly Pro Cys Arg Ala Ala His Pro Arg Trp Phe Phe Asn Ile

Phe Thr Arg Gln Cys Glu Glu Phe Ile Tyr Gly Gly Cys Glu Gly Asn Gln Asn Arg Phe Glu Ser Leu Glu Glu Cys Lys Lys Met Cys Thr Arg Asp (SEQ ID NO:3).

Plasma kallikrein inhibitor can be full-length antibodies (e.g., an IgG (e.g., an IgG1, IgG2, IgG3, IgG4), IgM, IgA (e.g., IgA1, IgA2), IgD, and IgE) or can include only an antigen-binding fragment (e.g., a Fab, F(ab')2 or scFv fragment). The binding protein can include two heavy chain immunoglobulins and two light chain immunoglobulins, or can be a single chain antibody. Plasma kallikrein inhibitor can be recombinant proteins such as humanized, CDR grafted, chimeric, deimmunized, or in vitro generated antibodies, and may optionally include constant regions derived from human germline immunoglobulin sequences. In one embodiment, the plasma kallikrein inhibitor is a monoclonal antibody.

Exemplary plasma kallikrein binding proteins are disclosed in U.S. Publication No. 20120201756, the entire contents of which are incorporated herein by reference. In some embodiments, the kallikrein binding protein is an antibody (e.g., a human antibody) having the light and/or heavy chains of antibodies selected from the group consisting of M162-A04, M160-G12, M142-H08, X63-G06, X101-A01 (also referred to as DX-2922), X81-B01, X67-D03, X67-G04, X81-B01, X67-D03, X67-G04, X115-B07, X115-D05, X115-E09, X115-H06, X115-A03, X115-D01, X115-F02, X124-G01 (also referred to herein as DX-2930 or lanadelumab), X115-G04, M29-D09, M145-D11, M06-D09 and M35-G04. In some embodiments, the plasma kallikrein binding protein competes with or binds the same epitope as M162-A04, M160-G12, M142-H08, X63-G06, X101-A01 (also referred to herein as DX-2922), X81-B01, X67-D03, X67-G04, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04. In some embodiments, the plasma kallikrein binding protein is lanadelumab. See US Publication No. 20110200611 and US Publication No. 20120201756, which are incorporated by reference herein.

An example of a plasma kallikrein inhibitory antibody is lanadelumab. The amino acid sequences of the heavy chain and light chain variable regions of lanadelumab are provided below with the CDR regions identified in boldface and underlined.

```
Lanadelumab heavy chain variable region sequence
                                            (SEQ ID NO: 4)
EVQLLESGGG LVQPGGSLRL SCAASGFTFS

HYIMMWVRQA PGKGLEWVSG IYSSGGITVY

ADSVKGRFTI SRDNSKNTLY LQMNSLRAED

TAVYYCAYRR IGVPRRDEFD IWGQGTMVTV

SS

Lanadelumab light chain variable region sequence
                                            (SEQ ID NO: 5)
DIQMTQSPS TLSASVGDRV TITCRASQSI

SSWLAWYQQK PGKAPKLLIY KASTLESGVP

SRFSGSGSGT EFTLTISSLQ PDDFATYYCQ

QYNTYWTFGQ GTKVEI
```

In some embodiments, a plasma kallikrein inhibitor can have about 85%, 90%, 91%, 92%, 93%, 94%, 95%, 96%, 97%, 98%, 99% or higher sequence identity to a plasma kallikrein inhibitor described herein. In some embodiments, a plasma kallikrein inhibitor can have about 85%, 90%, 91%, 92%, 93%, 94%, 95%, 96%, 97%, 98%, 99% or higher sequence identity in the HC and/or LC framework regions (e.g., HC and/or LC FR 1, 2, 3, and/or 4) to a plasma kallikrein inhibitor described herein. In some embodiments, a plasma kallikrein inhibitor can have about 85%, 90%, 91%, 92%, 93%, 94%, 95%, 96%, 97%, 98%, 99% or higher sequence identity in the HC and/or LC CDRs (e.g., HC and/or LC CDR1, 2, and/or 3) to a plasma kallikrein inhibitor described herein. In some embodiments, a plasma kallikrein inhibitor can have about 85%, 90%, 91%, 92%, 93%, 94%, 95%, 96%, 97%, 98%, 99% or higher sequence identity in the constant region (e.g., CH1, CH2, CH3, and/or CL1) to a plasma kallikrein inhibitor described herein.

In some aspects, a small molecule binds and inhibits the active form of plasma kallikrein.

Bradykinin B2 Receptor Inhibitors

In some embodiments, a bradykinin B2 receptor inhibitor (e.g., antagonist) is administered to a subject. Exemplary bradykinin B2 receptor antagonists include icatibant (Firazyr®), which is a peptidomimetic drug containing 10 amino acids which block binding of native bradykinin to the bradykinin B2 receptor.

C1-INH Replacement Agents

In some embodiment, a C1 esterase inhibitor (C1-INH), such as a replacement C1-INH agent is administered to a subject. Exemplary C1-INH replacement agents are publicly available and include, for example, human plasma-derived C1-INH, e.g. Berinert® and CINRYZE®.

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: Identification of Metabolites Differentially Present in Samples from HAE Patients Compared to Healthy Individuals To investigate novel metabolic biomarkers of hereditary angioedema, an analysis was performed comparing the metabolite composition of plasma samples obtained from patients with HAE to the metabolite composition of samples obtained from healthy individuals. Citrated plasma was collected from 20 healthy individuals and 20 patients having HAE during disease quiescence ("basal") and during an edematous attack ("attack"). The samples were subjected to a validated liquid chromatography-mass spectrometry (LC-MS) methodology to detect metabolites present in the samples. The analyses detected 1069 different plasma metabolites. The abundance of each metabolite was compared across the samples and subjected to statistical analysis.

As shown in Table 3, 187 different metabolites were differentially present in samples from HAE patients at basal state as compared to healthy individuals (73 were elevated, 114 were reduced); 156 different metabolites were differentially present in samples from HAE patients during an attack as compared to healthy individuals (51 were elevated, 105 were reduced); and 59 different metabolites were differentially present in samples from HAE patients during an attack as compared to HAE patients at basal state (25 were elevated during an attack, 34 were reduced during an attack).

TABLE 3

Summary of the metabolic analysis

| Summary Counts | Matched Pairs t-test | | Welch's Two Sample Test | | | |
|---|---|---|---|---|---|---|
| | Attack Basal | | Attack Normal | | Attack Normal | |
| Total number of biochemical with p ≤ 0.05 | 59 | | 156 | | 187 | |
| Biochemicals (↑↓) | 25 | 34 | 51 | 105 | 73 | 114 |

A random forest analysis indicated separation of HAE patients from healthy individuals with 78% classification accuracy (FIG. 1, panel A) and separation of HAE patients at basal state from HAE patients during an attack with 20% classification accuracy (FIG. 1, panel B).

Metabolomic Analysis Comparing Samples from HAE Patients to Healthy Individuals

The metabolomic comparison of samples from HAE patients and healthy individuals identified several potential metabolites that exhibit disease specific differences in the levels detected in plasma samples. For example, the neurotransmitter serotonin was found to be significantly elevated (P<0.05 Welch's two-sample t-tests) in plasma samples from HAE patients as compared to plasma samples from healthy individuals and specifically elevated during an HAE attack (Table 4; FIG. 2, panel A). Tryptophan, a serotonin precursor, was found to be decreased in plasma samples from HAE patients as compared to plasma samples from healthy individuals, further indicating serotonin metabolism is altered during HAE. Other metabolites involved in the production of serotonin (e.g., indolelactate and indolepropionate) were also found to be significantly different between HAE patients and healthy individuals (Table 4).

TABLE 4

Metabolites involved in the production of serotonin

| Biochemical | Attack Basal | Attack Normal | Basal Normal |
|---|---|---|---|
| tryptophan | 1.04 | 0.87 | 0.86 |
| indolelactate | 0.94 | 0.76 | 0.84 |
| indolepropionate | 1.58 | 0.7 | 0.78 |
| kynurenine | 1.05 | 1.07 | 1.05 |
| kynurenate | 1.05 | 1.07 | 1.17 |
| serotonin | 3.89 | 5.63 | 5.21 |

Serotonin is a neurotransmitter and a vasoactive amine that acts on the central nervous system, gastrointestinal tract, and blood platelets and is involved in regulating vascular tone. When serotonin levels were sorted based on HAE attack rates, it was observed that serotonin levels were highest in patients having more frequent HAE attacks (>2 attacks per month) (FIG. 2, panel B). Consequently, detecting serotonin levels may be useful for identifying patients with more active disease or patients whose disease is less likely to be controlled by therapy.

Several metabolites associated with fatty acid amide hydrolase (FAAH) activity were significantly increased in samples from patients with HAE, suggesting reduced fatty acid amide hydrolase activity in HAE patients (Table 5). For example, palmitic amide, oleamide, and linoleamide (18:2n6) were significantly elevated in HAE plasma as compared to healthy plasma (Table 5).

TABLE 5

Metabolites associated with fatty acid amide hydrolase (FAAH) activity

| Biochemical | Attack Basal | Attack Normal | Basal Normal |
|---|---|---|---|
| palmitic amide | 1.53 | 3.21 | 2.98 |
| oleamide | 3.57 | 13.73 | 6.7 |
| Linoleamide (18:2n6) | 3.81 | 10.51 | 7.71 |

Several lipid peroxide markers including 9/13-HODE, 9,10-DiHOME, 12,13-DiHOME and 19, 20 DiHDPA were found to be reduced in samples from HAE patients compared to healthy individuals (Table 6). This is consistent with decreased membrane associated oxidative stress predicted in patients with HAE.

TABLE 6

Lipid peroxide biomarkers

| Biochemical | Attack Basal | Attack Normal | Basal Normal |
|---|---|---|---|
| 13-HODE + 9-HODE | 1.93 | 0.67 | 0.58 |
| 12,13-DiHOME | 1.14 | 0.44 | 0.59 |
| 9,10-DiHOME | 0.91 | 0.47 | 0.67 |
| 12-HETE | 2.08 | 1.48 | 1.24 |

The lipid bound antioxidant gamma/beta-tocopherol was also found to have significantly elevated levels in the samples from HAE patients (Table 7).

TABLE 7

Metabolites with antioxidant properties

| Biochemical | Attack Basal | Attack Normal | Basal Normal |
|---|---|---|---|
| ascorbate (Vitamin C) | 2.78 | 0.7 | 0.64 |
| gamma-tocopherol/beta-tocopherol | 1.09 | 1.45 | 1.47 |

The metabolomic data further suggested that sulfur metabolism and steroid metabolism may be involved in HAE. As shown in Table 8, many metabolites associated with sulfur metabolism were detected at elevated levels, including N-acetylmethionine, methionine sulfone, S-adenosylhomocysteine (SAH), cystine, and cysteine sulfinic acid. Several steroid metabolites, including cortisol, were detected at reduced levels in HAE patients relative to healthy individuals (Table 9).

TABLE 8

Metabolites associated with sulfur metabolism

| Biochemical | Attack Basal | Attack Normal | Basal Normal |
|---|---|---|---|
| methionine | 1.1 | 0.92 | 0.91 |
| N-acetylmethionine | 1.1 | 1.3 | 1.24 |
| Methionine sulfone | 1 | 1.36 | 1.41 |
| S-adenosylhomocysteine (SAH) | 1.11 | 1.53 | 1.35 |
| Alpha-ketobutyrate | 1.09 | 1.25 | 1.29 |
| cystine | 0.97 | 1.21 | 1.26 |
| Cysteine sulfinic acid | 0.9 | 3.13 | 3.99 |

TABLE 8-continued

Metabolites associated with sulfur metabolism

| Biochemical | Attack Basal | Attack Normal | Basal Normal |
|---|---|---|---|
| hypotaurine | 1.09 | 1.12 | 1.07 |
| taurine | 1.24 | 1.52 | 1.17 |
| cysteine-glutathione disulfide | 1.15 | 0.89 | 0.81 |
| cys-gly, oxidized | 1.19 | 1.09 | 0.9 |

These results indicate that any of the metabolites identified in the metabolomics study can be used as biomarkers to distinguish between samples from patients with HAE from healthy individuals. Furthermore, this study identified anti-inflammatory, oxidative stress, and steroid metabolism pathways as being altered in HAE patients. These pathways may provide a potential source for novel biomarkers.

Metabolomic Analysis Comparing Samples from HAE Patients at Basal State Vs. During Attack The metabolomics analysis also identified several metabolites that were present at different levels between patients having HAE at basal state compared to patients having HAE during an attack. Corticosterone, an intermediate in the formation of aldosterone, was found to be significantly reduced during an HAE attack (Table 9). Additionally, several polyunsaturated fatty acids were significantly elevated during an attack as compared to during basal state, including eicosapentaenoate, mead acid, and stearidonate (Table 10). Finally, it was observed that two metabolic precursors of coenzyme A cofactor (nicotinamide and pantothenate) were significantly elevated during an attack as compared to at basal state (Table 11).

TABLE 9

Metabolites involved in steroid metabolism

| Biochemical | Attack Basal | Attack Normal | Basal Normal |
|---|---|---|---|
| pregnenolone sulfate | 1.24 | 0.62 | 0.57 |
| 5alpha-pregnan-3beta, 20beta-diol monosulfate (1) | 1.25 | 0.24 | 0.34 |
| pregnen-diol disulfate | 0.94 | 0.67 | 0.72 |
| pregn steroid monosulfate | 1.11 | 0.69 | 0.74 |
| pregnanediol-3-glucuronide | 1.23 | 0.33 | 0.43 |
| cortisol | 1.81 | 0.67 | 0.59 |
| corticosterone | 0.89 | 0.89 | 1.11 |
| cortisone | 1.18 | 0.74 | 0.72 |
| dehydroisoandrosterone (DHEA-S) | 1.04 | 0.69 | 0.69 |
| 16a-hydroxy DHEA 3-sulfate | 0.82 | 0.68 | 0.93 |
| epiandrosterone sulfate | 1.18 | 0.66 | 0.61 |
| androsterone sulfate | 1.12 | 0.58 | 0.56 |
| 4-androsten-3beta, 17beta-diol monosulfate (1) | 1.1 | 0.82 | 0.76 |
| 4-androsten-3beta, 17beta-diol monosulfate (2) | 0.99 | 0.56 | 0.58 |
| 4-androsten-3alpha, 17alpha-diol monosulfate (2) | 1.16 | 0.83 | 0.89 |
| 4-androsten-3alpha, 17alpha-diol monosulfate (3) | 1.04 | 0.55 | 0.55 |
| 4-androsten-3beta, 17beta-diol disulfate (1) | 1.04 | 0.52 | 0.52 |
| 4-androsten-3beta, 17beta-diol disulfate (2) | 0.92 | 0.71 | 0.8 |
| 5alpha-androstan-3alpha, 17beta-diol monosulfate (1) | 1.15 | 0.69 | 0.62 |
| 5alpha-androstan-3alpha, 17alpha-diol monosulfate | 1.19 | 0.59 | 0.55 |
| 5alpha-androstan-3beta, 17beta-diol monosulfate (2) | 1.17 | 0.82 | 0.72 |
| 5alpha-androstan-3beta, 17alpha-diol disulfate | 0.99 | 0.83 | 1.62 |

TABLE 9-continued

Metabolites involved in steroid metabolism

| Biochemical | Attack Basal | Attack Normal | Basal Normal |
|---|---|---|---|
| 5alpha-androstan-3alpha, 17beta-diol disulfate | 1.59 | 0.55 | 0.69 |
| 5alpha-androstan-3beta, 17beta-diol disulfate | 1.13 | 0.5 | 0.52 |
| andro steroid monosulfate (1) | 0.98 | 0.66 | 0.89 |
| etiocholanolone glucuronide | 1.14 | 0.72 | 0.82 |
| 5alpha-androstan-3alpha, 17beta-diol monosulfate (2) | 1 | 1.14 | 1.23 |
| Pregnanolone/allopregnanolone sulfate | 1.27 | 0.18 | 0.28 |

TABLE 10

Polyunsaturated fatty acids

| Biochemical | Attack Basal | Attack Normal | Basal Normal |
|---|---|---|---|
| eicosapentaenoate (EPA; 20:5n3) | 1.62 | 1.23 | 0.81 |
| mead acid (20:3n9) | 1.69 | 1.02 | 0.66 |
| Stearidonate (18:4n3) | 2.41 | 1.34 | 0.85 |

TABLE 11

Metabolic precursors of coenzyme A cofactor

| Biochemical | Attack Basal | Attack Normal | Basal Normal |
|---|---|---|---|
| Nicotinamide | 1.55 | 1 | 0.74 |
| Pantothenate | 1.22 | 0.88 | 0.77 |

These results indicated that these metabolites, for example, those having a significant fold change ratio can be used as reliable biomarkers for HAE and other diseases associated with the contact system, either taken alone or in combination.

The metabolomic data also provided novel insight into the pathobiology of HAE. For example, a subset of the metabolites were associated with edema, including serotonin and lipid amides; metabolites associated with oxidative stress, such as oxidative limits, gamma-/beta-tocopherol; and steroids. The analysis also provided insight into the pathobiology of HAE at basal state as compared to during an attack. For example, some of the differences between basal state and during an attack included anti-inflammatory lipid precursors, mineral corticoid (corticosterone), and regulators of water and salt balance.

The metabolomic analysis also identified many metabolites that were present at levels that differed between patients with HAE and healthy individuals, and between patients with HAE at basal state compared to during an attack. Any of the metabolites identified herein (e.g., metabolites having a significant fold change between HAE patients and healthy individuals), may be used as a biomarker (individually or in combination (biomarker set)) for diseases associated with the contact activation system, for example in methods for identifying patients who are at risk of a disease associated with the contact activation system (e.g., HAE), selecting a candidate for treatment, monitoring disease progression or disease state, assessing the efficacy of a treatment against a disease, determining a course of treatment, identifying whether a disease or disorder is associated with the contact activation system, and/or for research purposes, including, e.g., studying the mechanism of a disease, which may be relied upon for the development of new therapies.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the present disclosure to adapt it to various usages and conditions. Thus, other embodiments are also within the claims.

Equivalents and Scope

Those skilled in the art will recognize, or be able to ascertain using no more than routine experimentation, many equivalents to the specific embodiments of the present disclosure described herein. The scope of the present disclosure is not intended to be limited to the above description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The present disclosure includes embodiments in which exactly one member of the group is present in, employed in, or otherwise relevant to a given product or process. The present disclosure includes embodiments in which more than one, or all of the group members are present in, employed in, or otherwise relevant to a given product or process.

Furthermore, the present disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the present disclosure, or aspects of the present disclosure, is/are referred to as comprising particular elements and/or features, certain embodiments of the present disclosure or aspects of the present disclosure consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the present disclosure, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the present disclosure can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

What is claimed is:

1. A method comprising:
   (i) providing a biological sample obtained from a subject after a treatment or during a course of treatment for hereditary angioedema (HAE);
   (ii) measuring the level of a metabolite biomarker set in the biological sample, wherein the metabolite biomarker set comprises at least one metabolite biomarker selected from the group consisting of serotonin; tryptophan; indolelactate; indolepropionate; gamma-/beta-tocopherol; ascorbate; palmitic amide; oleamide; linoleamide; 9-hydroxyoctadecadienoic acid (9-HODE); 13-hydroxyoctadecadienoic acid (13-HODE); 9,10-di-hydroxy-12Z-octadecenoic acid (9,10-DiHOME); 12,13-dihydroxy-9Z-octadecenoic acid (12,13-DiHOME); 19,20-dihydroxy -4Z,7Z,10Z,13Z,16Z-docosapentaenoic acid (19,20 DiHDPA); N-acetylmethionine; methionine sulfone; S-adenosylhomocysteine; cysteine; cysteine sulfinic acid, pregnenolone sulfate; 5 alpha -pregnan-3beta,20beta-diol monosulfate; pregnen-diol disulfate; pregn steroid monosulfate; pregnanediol-3-glucuronide; corticosterone; cortisone; dehydroisoandrosterone sulfate (DHEA-S); 16a-hydroxy DHEA 3-sulfate; epiandrosterone sulfate; androsterone sulfate; 4-androsten -3beta, 17beta-diol monosulfate; 4-androsten-3alpha, 17alpha-diol monosulfate; 4-androsten -3beta, 17beta-diol disulfate; 5alpha-androstan-3alpha, 17alpha-diol monosulfate; 5alpha -androstan-3beta, 17-betadiol disulfate; andro steroid monosulfate; etiocholanolone glucuronide; pregnanolone/alloprenanolone sulfate; eicosapentaenoate; mead acid; stearidonate; nicotinamide; and pantothenate;
   (iii) identifying the subject as not responsive to the treatment if the level of the metabolite biomarker set deviates from the level of a corresponding metabolite biomarker set in a control sample; and
   (iv) administering to the subject identified in (iii) a therapeutic agent for treating HAE.

2. The method of claim 1, wherein the biomarker set consists of 2-10 metabolite biomarkers.

3. The method of claim 1, wherein the biological sample is a serum sample or a plasma sample.

4. The method of claim 1, wherein the HAE is type I HAE or type II HAE.

5. The method of claim 1, wherein the metabolite biomarker set comprises:
   (a) serotonin;
   (b) a metabolite associated with fatty acid amide hydrolase activity;
   (c) a lipid peroxide;
   (d) a metabolite involved in sulfur metabolism;
   (e) a metabolite involved in steroid metabolism;
   (f) a fatty acid; and/or
   (g) a cofactor precursor.

6. The method of claim 5, wherein
   the metabolite biomarker associated with fatty acid amide hydrolase activity is palmitic amide, oleamide, or linoleamide;
   the lipid peroxide is 9-hydroxyoctadecadienoic acid (9-HODE), 13-hydroxyoctadecadienoic acid (13-HODE), 9,10-di-hydroxy-12Z-octadecenoic acid (9,10-DiHOME), 12,13-dihydroxy-9Z-octadecenoic acid (12,13-DiHOME), or 19,20-dihydroxy -4Z,7Z,10Z,13Z,16Z-docosapentaenoic acid (19,20 DiHDPA);
   the metabolite involved in sulfur metabolism is N-acetylmethionine, methionine sulfone, S-adenosylhomocysteine, cystine, or cysteine sulfinic acid;
   the metabolite involved in steroid metabolism is selected from the group consisting of pregnenolone sulfate; 5 alpha-pregnan-3beta,20beta-diol monosulfate; pregnen-diol disulfate; pregn steroid monosulfate; pregnanediol-3-glucuronide; cortisol; corticosterone; cortisone; dehydroisoandrosterone sulfate (DHEA-S); 16a-hydroxy DHEA 3-sulfate; epiandrosterone sulfate; androsterone sulfate; 4-androsten-3beta, 17beta-diol monosulfate; 4-androsten-3alpha, 17alpha-diol monosulfate; 4-androsten-3beta, 17beta-diol disulfate; 5alpha-androstan -3alpha, 17alpha-diol monosulfate; 5alpha-androstan-3beta, 17-beta-diol disulfate; andro steroid monosulfate, etiocholanolone glucuronide; and pregnanolone/alloprenanolone sulfate;
   the fatty acid is eicosapentaenoate (EPA), mead acid, or stearidonate; and/or
   the cofactor precursor is nicotinamide or pantothenate.

7. The method of claim 1, wherein step (ii) involves mass spectrometry, chromatography, or an immunoassay.

8. The method of claim 7, wherein step (ii) involves mass spectrometry and the biological sample is subjected to a separation step prior to the mass spectrometry.

9. The method of claim 1, wherein the subject is a human patient.

10. The method of claim 1, wherein the therapeutic agent is a plasma kallikrein (pKal) inhibitor, a bradykinin 2 receptor (B2R) inhibitor, and/or a C1 esterase inhibitor.

11. The method of claim 10, wherein the pKal inhibitor is an anti-pKal antibody or an inhibitory peptide.

12. The method of claim 11, wherein the therapeutic agent is lanadelumab, ecallantide, icatibant, or human plasma-derived C1-INH.

13. The method of claim 1, wherein the subject is a human patient having a history of the disease.

14. The method of claim 13, wherein the metabolite biomarker set comprises one or more metabolite biomarkers selected from the group consisting of corticosterone, eicosapentaenoate, mead acid, stearidonate, nicotinamide, and pantothenate.

15. The method of claim 1, wherein the administering of (iv) comprises increasing a dosage of the therapeutic agent as compared to the treatment of (i).

16. The method of claim 1, wherein the administering of (iv) comprises increasing frequency of dosing the therapeutic agent as compared to the treatment of (i).

17. The method of claim 1, wherein the therapeutic agent of (iv) is a different therapeutic agent as the treatment of (i).

18. The method of claim 8, wherein the separation step comprises gas chromatography, liquid chromatography, or capillary electrophoresis.

* * * * *

SEQUENCE LISTING

```
<160> NUMBER OF SEQ ID NOS: 5

<210> SEQ ID NO 1
<211> LENGTH: 304
<212> TYPE: PRT
<213> ORGANISM: Homo sapiens

<400> SEQUENCE: 1

Met Ile Tyr Thr Met Lys Lys Val His Ala Leu Trp Ala Ser Val Cys
1               5                   10                  15

Leu Leu Leu Asn Leu Ala Pro Ala Pro Leu Asn Ala Asp Ser Glu Glu
            20                  25                  30

Asp Glu Glu His Thr Ile Ile Thr Asp Thr Glu Leu Pro Pro Leu Lys
        35                  40                  45
```

Leu Met His Ser Phe Cys Ala Phe Lys Ala Asp Asp Gly Pro Cys Lys
    50                  55                  60

Ala Ile Met Lys Arg Phe Phe Asn Ile Phe Thr Arg Gln Cys Glu
65                  70                  75                  80

Glu Phe Ile Tyr Gly Gly Cys Glu Gly Asn Gln Asn Arg Phe Glu Ser
                85                  90                  95

Leu Glu Glu Cys Lys Lys Met Cys Thr Arg Asp Asn Ala Asn Arg Ile
            100                 105                 110

Ile Lys Thr Thr Leu Gln Gln Glu Lys Pro Asp Phe Cys Phe Leu Glu
        115                 120                 125

Glu Asp Pro Gly Ile Cys Arg Gly Tyr Ile Thr Arg Tyr Phe Tyr Asn
    130                 135                 140

Asn Gln Thr Lys Gln Cys Glu Arg Phe Lys Tyr Gly Gly Cys Leu Gly
145                 150                 155                 160

Asn Met Asn Asn Phe Glu Thr Leu Glu Glu Cys Lys Asn Ile Cys Glu
                165                 170                 175

Asp Gly Pro Asn Gly Phe Gln Val Asp Asn Tyr Gly Thr Gln Leu Asn
            180                 185                 190

Ala Val Asn Asn Ser Leu Thr Pro Gln Ser Thr Lys Val Pro Ser Leu
        195                 200                 205

Phe Glu Phe His Gly Pro Ser Trp Cys Leu Thr Pro Ala Asp Arg Gly
    210                 215                 220

Leu Cys Arg Ala Asn Glu Asn Arg Phe Tyr Tyr Asn Ser Val Ile Gly
225                 230                 235                 240

Lys Cys Arg Pro Phe Lys Tyr Ser Gly Cys Gly Gly Asn Glu Asn Asn
                245                 250                 255

Phe Thr Ser Lys Gln Glu Cys Leu Arg Ala Cys Lys Lys Gly Phe Ile
            260                 265                 270

Gln Arg Ile Ser Lys Gly Gly Leu Ile Lys Thr Lys Arg Lys Arg Lys
        275                 280                 285

Lys Gln Arg Val Lys Ile Ala Tyr Glu Glu Ile Phe Val Lys Asn Met
    290                 295                 300

<210> SEQ ID NO 2
<211> LENGTH: 58
<212> TYPE: PRT
<213> ORGANISM: Homo sapiens

<400> SEQUENCE: 2

Arg Pro Asp Phe Cys Leu Glu Pro Pro Tyr Thr Gly Pro Cys Lys Ala
1               5                   10                  15

Arg Ile Ile Arg Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
        35                  40                  45

Glu Asp Cys Met Arg Thr Cys Gly Gly Ala
    50                  55

<210> SEQ ID NO 3
<211> LENGTH: 60
<212> TYPE: PRT
<213> ORGANISM: Artificial Sequence
<220> FEATURE:
<223> OTHER INFORMATION: Synthetic polypeptide

<400> SEQUENCE: 3

```
Glu Ala Met His Ser Phe Cys Ala Phe Lys Ala Asp Asp Gly Pro Cys
1               5                   10                  15

Arg Ala Ala His Pro Arg Trp Phe Phe Asn Ile Phe Thr Arg Gln Cys
                20                  25                  30

Glu Glu Phe Ile Tyr Gly Gly Cys Glu Gly Asn Gln Asn Arg Phe Glu
            35                  40                  45

Ser Leu Glu Glu Cys Lys Lys Met Cys Thr Arg Asp
        50                  55                  60
```

<210> SEQ ID NO 4
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 4

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
                20                  25                  30

Ile Met Met Trp Val Arg Gln Ala Pro Gly Lys Gly Leu Glu Trp Val
            35                  40                  45

Ser Gly Ile Tyr Ser Ser Gly Gly Ile Thr Val Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Tyr Arg Arg Ile Gly Val Pro Arg Arg Asp Glu Phe Asp Ile Trp
            100                 105                 110

Gly Gln Gly Thr Met Val Thr Val Ser Ser
        115                 120
```

<210> SEQ ID NO 5
<211> LENGTH: 105
<212> TYPE: PRT
<213> ORGANISM: Artificial Sequence
<220> FEATURE:
<223> OTHER INFORMATION: Synthetic polypeptide

<400> SEQUENCE: 5

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Lys Ala Ser Thr Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Thr Tyr Trp Thr
                85                  90                  95

Phe Gly Gln Gly Thr Lys Val Glu Ile
            100                 105
```